United States Patent
Brown et al.

(10) Patent No.: US 11,513,131 B2
(45) Date of Patent: Nov. 29, 2022

(54) LOW DENSITY LIPOPROTEIN TRIGLYCERIDES (LDL-TG) AS A BIOMARKER OF CARDIOVASCULAR DISEASE AND USES THEREOF

(71) Applicant: Global Genomics Group, LLC, Midlothian, VA (US)

(72) Inventors: Bradley O. Brown, Moseley, VA (US); Idean B. Marvasty, Atlanta, GA (US); Szilard Voros, Setauket, NY (US)

(73) Assignee: Global Genomics Group, LLC, Midlothian, VA (US)

( * ) Notice: Subject to any disclaimer, the term of this patent is extended or adjusted under 35 U.S.C. 154(b) by 0 days.

(21) Appl. No.: 16/253,743

(22) Filed: Jan. 22, 2019

(65) Prior Publication Data

US 2019/0227085 A1 Jul. 25, 2019

Related U.S. Application Data

(60) Provisional application No. 62/620,253, filed on Jan. 22, 2018.

(51) Int. Cl.
*G01N 33/92* (2006.01)

(52) U.S. Cl.
CPC ......... *G01N 33/92* (2013.01); *G01N 2405/02* (2013.01); *G01N 2800/32* (2013.01); *G01N 2800/50* (2013.01)

(58) Field of Classification Search
CPC . G01N 33/92; G01N 2800/32; G01N 2405/02
See application file for complete search history.

(56) References Cited

U.S. PATENT DOCUMENTS

| | | | | |
|---|---|---|---|---|
| 2015/0132834 A1* | 5/2015 | Ohta | ................. | C07K 1/14 435/272 |
| 2016/0202239 A1* | 7/2016 | Voros | ................. | A61K 31/616 514/165 |

OTHER PUBLICATIONS

Hlatky et al., "Criteria for evaluation of novel markers of cardiovascular risk: a scientific statement from the American Heart Association," Circulation, May 2009, 119(17): 2408-2416.

Li et al., "A blood-based proteomic classifier for the molecular characterization of pulmonary nodules," Sci. Transl. Med., Oct. 2013, 5(207): 207ra142.

Maurovich-Horvat et al., "The napkin-ring sign indicates advanced atherosclerotic lesions in coronary CT angiography," JACC Cardiovasc. Imaging, Dec. 2012, 5(12): 1243-1252.

Motoyama et al., "Multislice computed tomographic characteristics of coronary lesions in acute coronaiy syndromes," J. Am, Coll. Cardiol., Jul. 2007, 50(4):319-326.

Raff et al., "SCCT guidelines for the interpretation and reporting of coronary computed tomographic angiography," J. Cardiovasc. Comput. Tomogr., Mar.-Apr. 2009, 3(2):122-136.

Voros et al., "Precision phenotyping, panomics, and system-level bioinformatics to delineate complex biologies of atherosclerosis: rationale and design of the 'Genetic Loci and the Burden of Atherosclerotic Lesions," J. Cardiovasc. Comput. Tomogr., November-Dec. 2014, 8(6):442-451.

* cited by examiner

*Primary Examiner* — Ruth A Davis
(74) *Attorney, Agent, or Firm* — Fish & Richardson P.C.

(57) ABSTRACT

The invention, in some aspects, relates to methods for diagnosing cardiovascular disease, and/or detecting cardiovascular disease in a patient, and more particularly to methods of using blood-based biomarkers and their combinations to identify patients at risk of having cardiovascular disease (e.g., coronary atherosclerosis).

11 Claims, 7 Drawing Sheets

LOW DENSITY LIPOPROTEIN TRIGLYCERIDES (LDL-TG) AS A BIOMARKER OF CARDIOVASCULAR DISEASE AND USES THEREOF

CROSS-REFERENCE TO RELATED APPLICATIONS

This application claims priority to U.S. Provisional Patent Application Ser. No. 62/620,253, filed Jan. 22, 2018; the entire contents of which are herein incorporated by reference.

TECHNICAL FIELD

This invention relates to non-invasive methods for diagnosing cardiovascular disease, and/or detecting cardiovascular disease in a patient, and more particularly to methods of using blood-based biomarkers and their combinations to identify patients with cardiovascular disease (e.g. coronary atherosclerosis), at risk of having cardiovascular disease, or high likelihood of adverse cardiovascular events (including, but not limited to death, heart attack [myocardial infarction], angina, etc.)

BACKGROUND

Cardiovascular disease (CVD) remains the leading cause of morbidity and mortality both in the United States and worldwide. Based on the 2014 Heart Disease and Stroke Update by the American Heart Association (AHA), 83.6 million American adults have at least one type of CVD (>1 in 3 prevalence). Of these adults, 15.4 million suffer from coronary heart disease (CHD), with the following breakdown: myocardial infarction (MI): 7.6 million and angina pectoris (AP): 7.8 million. It is estimated that by 2030, 43.9% of the US population will have some form of CVD.

The underlying cause of CVD is atherosclerotic coronary artery disease (ASCAD), which begins with the development of an atherosclerotic plaque in the coronary arterial vasculature. Atherosclerosis is of unquestionable importance, in terms of human health and societal cost. It is responsible for coronary artery disease (CAD) and cerebrovascular disease, both of which are leading causes of morbidity and mortality worldwide. Atherosclerosis is also responsible for peripheral arterial disease, a leading medical cause of limb-loss.

SUMMARY

In one aspect, the disclosure provides non-invasive methods of predicting the likelihood and/or risk of a human subject for having cardiovascular disease (e.g., atherosclerotic coronary artery disease (ASCAD)).

Provided herein are methods of predicting the presence, and/or the risk of cardiovascular disease in a human subject that include: determining the levels of LDL-TG in a blood sample obtained from a subject; and identifying the subject as having, or being at risk of having cardiovascular disease if the level of LDL-TG is elevated as compared to a control level.

In some embodiments of any the methods described herein, the method can further include determining the level of at least one analyte in the blood sample obtained from the subject, wherein the at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA), and identifying the subject as having or being at risk of having cardiovascular disease if the levels of LDL-TG and the at least one analyte are both elevated as compared to a control level.

In some embodiments, determining comprises determining the levels of at least two analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having or being at risk of having cardiovascular disease if at least one of the two levels is elevated as compared to control level(s). In some embodiments, the subject is identified as having or being at risk of having cardiovascular disease if both levels are elevated as compared to control levels.

In some embodiments, determining comprises determining the levels of at least three analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having or being at risk of having cardiovascular disease if at least one of the three levels is elevated as compared to control level(s). In some embodiments, the subject is identified as having being at risk of having cardiovascular disease if all three levels are elevated as compared to control levels.

In some embodiments, determining comprises determining the levels of at least four analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having or being at risk of having cardiovascular disease if at least one of the four levels is elevated as compared to control level(s). In some embodiments, the subject is identified as having or being at risk of having cardiovascular disease if all four levels are elevated as compared to control levels. In some embodiments, determining comprises determining the level of at least one of triglycerides, IL-6, SDMA, apoB48, POA, sdLDL, ALP and ADMA.

In some embodiments, POA is POA (16:1n7).

In some embodiments, the method further includes administering a treatment for cardiovascular disease to the subject identified as having or being at risk of having cardiovascular disease. In some embodiments, the treatment is selected from the group consisting of: a statin drug, a fibrate, an intestinal cholesterol absorption inhibitor, a peroxisome proliferator-activated receptor (PPAR)-alpha agonist, a PPAR gamma agonist, niacin, a bile acid sequestrant, ezetimibe, a proprotein convertase subtilisin/kexin type 9 (PCSK9) inhibitor, a cholesterylester transfer protein (CETP) inhibitor, an ATP citrate lyase (ACLY) drug, a bromodomain and extraterminal (BET) inhibitor and lifestyle interventions. In some embodiments, the treatment is a PCSK9 inhibitor and the PCSK9 inhibitor is alirocumab or evelocumab. In some embodiments, the treatment is an ACLY drug and the ACLY drug is bempedoic acid. In some embodiments, the treatment is a BET inhibitor and the BET inhibitor is RVX-208.

In some embodiments, the control level is a threshold level or a level in a healthy subject or a population of healthy subjects.

In some embodiments, the subject presents with symptoms of cardiovascular disease comprising chest pain, angina, angina equivalent, dyspnea, or dyspnea on exertion.

In some embodiments, the subject presents with risk factors associated with cardiovascular disease selected from the group consisting of: male gender, hypertension, dyslipidemia, diabetes, and a family history of coronary artery disease. In some embodiments, the subject has no diagnosed history of cardiovascular disease.

In some embodiments of any of the methods described herein, the determining step is performed using mass spectrometry (MS).

Also provided herein are methods of diagnosing cardiovascular disease in a human subject that include: determining the level of LDL-TG in a blood sample obtained from a subject; and identifying the subject as having cardiovascular disease if the level of LDL-TG is elevated as compared to a control level.

In some embodiments, the method further includes determining the level of at least one analyte in the blood sample obtained from the subject, wherein the at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA), and identifying the subject as having cardiovascular disease if the levels of LDL-TG and the at least one analyte are both elevated as compared to a control level.

In some embodiments, determining comprises determining the levels of at least two analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having cardiovascular disease if at least one of the two levels is elevated as compared to control level(s). In some embodiments, the subject is identified as having cardiovascular disease if both levels are elevated as compared to control levels.

In some embodiments, determining comprises determining the levels of at least three analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having cardiovascular disease if at least one of the three levels is elevated as compared to control level(s). In some embodiments, the subject is identified as having cardiovascular disease if all three levels are elevated as compared to control levels.

In some embodiments, determining comprises determining the levels of at least four analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having cardiovascular disease if at least one of the four levels is elevated as compared to control level(s). In some embodiments, the subject is identified as having cardiovascular disease if all four levels are elevated as compared to control levels.

In some embodiments, determining comprises determining the level of at least one of triglycerides, IL-6, SDMA, apoB48, POA, sdLDL, ALP and ADMA. In some embodiments, POA is POA (palmitoleic acid; 16:1n7).

In some embodiments, the method further includes administering a treatment for cardiovascular disease to the subject identified as having cardiovascular disease. In some embodiments, the treatment is selected from the group consisting of: a statin drug, a fibrate, an intestinal cholesterol absorption inhibitor, a peroxisome proliferator-activated receptor (PPAR)-alpha agonist, a PPAR gamma agonist, niacin, a bile acid sequestrant, ezetimibe, a proprotein convertase subtilisin/kexin type 9 (PCSK9) inhibitor, a cholesterylester transfer protein (CETP) inhibitor, an ATP citrate lyase (ACLY) drug, a bromodomain and extraterminal (BET) inhibitor and lifestyle interventions.

Also provided herein are methods of monitoring cardiovascular disease in a human subject that include: (a) providing a first blood sample obtained from a subject at a first time point; (b) determining the levels of at least one analyte in the first biological sample, wherein the at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA); (c) providing a second blood sample obtained from the subject obtained at a second time point after the first time point, and performing step (b) on the second blood sample; and (d) identifying the subject as having improving or static cardiovascular disease if the level of LDL-TG at the second time point is not elevated as compared to the first time point.

In some embodiments, the method further includes determining the level of at least one analyte in the blood sample obtained from the subject, wherein the at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA), and identifying the subject as having improving or static cardiovascular disease if the level of LDL-TG and the at least one analyte at the second time point are not elevated as compared to the levels of the LDL-TG and the at least one analyte at the first time point.

In some embodiments, determining comprises determining the levels of at least two analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having improving or static cardiovascular disease if the level of LDL-TG and at least one of the two analytes at the second time point are not elevated as compared to the levels of the LDL-TG and the at least one analyte at the first time point. In some embodiments, the subject is identified as having improving or static cardiovascular disease if both levels are elevated as compared to control levels.

In some embodiments, determining comprises determining the level of at least one of triglycerides, IL-6, SDMA, apoB48, POA, sdLDL, ALP and ADMA.

Also provided herein are kits that include: reagents suitable for determining levels of LDL-TG in a blood sample obtained from a subject. In some embodiments of any of the kits described herein, the kits can further include reagents suitable for determining the levels of at least one analyte, wherein the at least one analyte is selected from the group consisting of: triglycerides, total cholesterol, LDL-cholesterol, HDL-cholesterol, apoB, IL-6, SDMA, apoB48, POA, sd-LDL, ALP and ADMA. In some embodiments, the at least one analyte is selected from the group consisting of: triglycerides, IL-6, SDMA, apoB48, POA, sdLDL, ALP and ADMA.

Also provided herein are methods of screening a subject (e.g., a human subject) for cardiovascular disease that include: atherosclerotic coronary artery disease, sudden cardiac death, myocardial infarction, etc.

Also provided herein are methods of diagnosing a subject (e.g., a human subject) for cardiovascular disease that include: atherosclerotic coronary artery disease, sudden cardiac death, myocardial infarction, etc.

Also provided herein are methods of risk stratification of a subject (e.g., a human subject) for cardiovascular disease that include: atherosclerotic coronary artery disease, sudden cardiac death, myocardial infarction, etc.

In some embodiments of any of the methods described herein, the method includes identifying and selecting a diagnostic workup for cardiovascular disease. In some embodiments of any of the methods described herein where the subject has been identified as having or at risk of having cardiovascular disease, the method further includes performing a coronary artery calcium scan, a cardiac computed tomography (CT) scan, an exercise stress test, myocardial perfusion imaging (e.g., nuclear cardiology, echocardiography, CT scanning, magnetic resonance imaging (MRI) scanning etc.) and/or a myocardial stress functional test (e.g., nuclear cardiology, echocardiography, CT scanning, magnetic resonance imaging (MRI) scanning etc.).

In some embodiments of any of the methods described herein, the method further includes selecting and administering a treatment identified as in need thereof. In some embodiments, the treatment is a statin drug, fibrates, intestinal cholesterol absorption inhibitors, peroxisome proliferator-activated receptor (PPAR)-alpha agonists, PPAR gamma agonists, niacin, bile acid sequestrants, ezetimibe, proprotein convertase subtilisin/kexin type 9 (PCSK9) inhibitors (e.g., alirocumab (Praluent®), cholesterylester transfer protein (CETP) inhibitors, ATP citrate lyase (ACLY) drugs (e.g., bempedoic acid), bromodomain and extraterminal (BET) inhibitors (e.g., RVX-208) or lifestyle interventions (e.g., diet and physical activity).

As used herein, the term "biological sample" or "sample" refers to a sample obtained or derived from a subject. By way of example, the sample may be selected from the group consisting of body fluids, blood, whole blood, plasma, serum, mucus secretions, urine or saliva. In some embodiments the sample is, or comprises a blood sample. The preferred biological source for detection of the biomarkers is a blood sample, a serum sample or a plasma sample.

The term "subject" as used herein refers to a mammal. A subject therefore refers to, for example, dogs, cats, horses, cows, pigs, guinea pigs, humans and the like. When the subject is a human, the subject may be referred to herein as a patient. The subject can be symptomatic (e.g., the subject presents symptoms associated with cardiovascular disease, such as, for example, chest pain, angina, angina equivalent, dyspnea, or dyspnea on exertion; and/or presents risk factors associated with coronary artery disease, such as, for example, male gender, hypertension, dyslipidemia, diabetes, post-menopausal state in females, smoking, or a family history of coronary artery disease), or the subject can be asymptomatic (e.g., the subject does not present symptoms associated with cardiovascular disease).

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

In some embodiments, the reference sample is obtained from at least one individual not suffering from cardiovascular disease. In some other embodiments, the reference sample is obtained from at least one individual previously diagnosed as having cardiovascular disease (e.g., atherosclerotic coronary artery disease (ASCAD) or a coronary atherosclerotic plaque). In some embodiments, the reference sample comprises a predetermined, statistically significant reference analyte levels. In some embodiments, the methods further comprise performing a comparison between the measured levels of one or more analytes in the biological sample with one or more reference samples, wherein the reference sample is obtained from a matched (e.g., age, gender, etc.) human subject.

In some embodiments, the determining step is performed using a gradient boosting algorithm. In some embodiments, the determining step is performed using generalized linear modeling.

The terms "decrease", "reduction" or 'down-regulated" are all used herein generally to mean a decrease by a statistically significant amount. In some embodiments, "decrease", "reduction" or 'down-regulated" refer to a decrease by at least 10% as compared to a reference level (e.g., at least about 20%, at least about 30%, at least about 40%, at least about 50%, at least about 60%, at least about 70%, at least about 80%, at least about 90% or up to and including a 100% decrease (i.e. absent level as compared to a reference sample), between 10-100%, between 10-90%, between 10-80%, between 10-70%, between 10-60%, between 10-50%, between 10-40%, between 10-30%, between 10-20%, between 20-100%, between 20-90%, between 20-80%, between 20-70%, between 20-60%, between 20-50%, between 20-40%, between 20-30%, between 30-100%, between 30-90%, between 30-80%, between 30-70%, between 30-60%, between 30-50%, between 30-40%, between 40-100%, between 40-90%, between 40-80%, between 40-70%, between 40-60%, between 40-50%, between 50-100%, between 50-90%, between 50-80%, between 50-70%, between 50-60%, between 60-100%, between 60-90%, between 60-80%, between 60-70%, between 70-100%, between 70-90%, between 70-80%, between 80-100%, between 80-90%, or between 90-100%). In some embodiments, "decrease", "reduction" or 'down-regulated" refer to a decrease of at least about a 0.5-fold (e.g., at least about a 1.0-fold, at least about a 1.2-fold, at least about a 1.5-fold, at least about a 2-fold, at least about a 3-fold, at least about a 4-fold, at least about a 5-fold or at least about a 10-fold decrease) as compared to a reference level.

The terms "increased" or "up-regulated" are all used herein to generally mean an increase by a statistically significant amount. In some embodiments, the terms "increased" or "up-regulated" refer to an increase of at least 10% as compared to a reference level (e.g., at least about 20%, at least about 30%, at least about 40%, at least about 50%, at least about 60%, at least about 70%, at least about 80%, at least about 90% or up to and including a 100% increase; between 10-100%, between 10-90%, between 10-80%, between 10-70%, between 10-60%, between 10-50%, between 10-40%, between 10-30%, between 10-20%, between 20-100%, between 20-90%, between 20-80%, between 20-70%, between 20-60%, between 20-50%, between 20-40%, between 20-30%, between 30-100%, between 30-90%, between 30-80%, between 30-70%, between 30-60%, between 30-50%, between 30-40%, between 40-100%, between 40-90%, between 40-80%, between 40-70%, between 40-60%, between 40-50%, between 50-100%, between 50-90%, between 50-80%, between 50-70%, between 50-60%, between 60-100%, between 60-90%, between 60-80%, between 60-70%, between 70-100%, between 70-90%, between 70-80%, between 80-100%, between 80-90%, or between 90-100%). In some embodiments, the terms "increased" or "up-regulated" refer to an increase of at least about a 0.5-fold (e.g., at least about a 1.0-fold, at least about a 1.2-fold, at least about a 1.5-fold, at least about a 2-fold, at least about a 3-fold, at least about a 4-fold, at least about a 5-fold, at least about a 10-fold increase).

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 5A is a cumulative incidence curve for the presence of coronary atherosclerosis as a function of apoB in all subjects.

FIG. 5B is a cumulative incidence curve for the presence of coronary atherosclerosis as a function of LDL-cholesterol in all subjects.

FIG. 5C is a cumulative incidence curve for the presence of coronary atherosclerosis as a function of LDL-triglycerides in all subjects.

FIG. 5D is a cumulative incidence curve for the presence of coronary atherosclerosis as a function of apoB, excluding statin-treated subjects.

FIG. 5E is a cumulative incidence curve for the presence of coronary atherosclerosis as a function of LDL-cholesterol, excluding statin-treated subjects.

FIG. 5F is a cumulative incidence curve for the presence of coronary atherosclerosis as a function of LDL-triglycerides, excluding statin-treated subjects.

DETAILED DESCRIPTION

Figure 1:
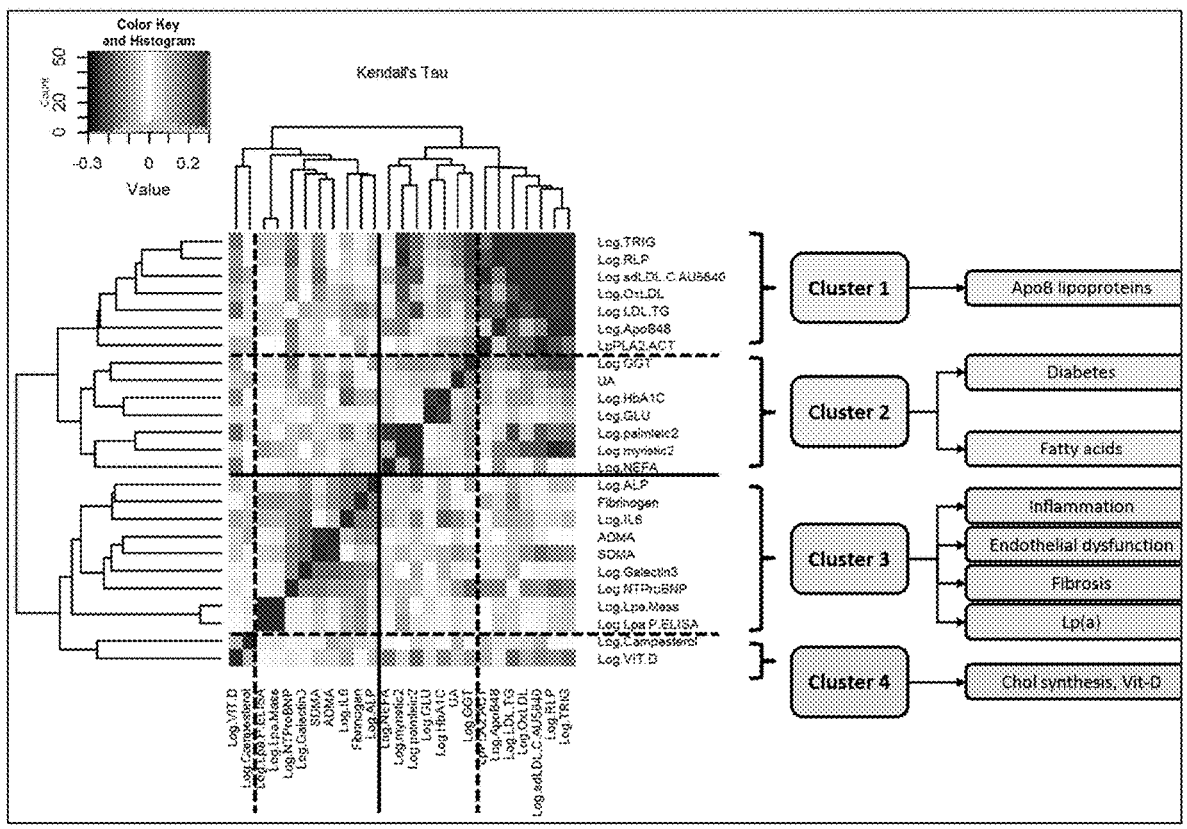
FIG. 1 is an exemplary clustogram showing the results of an unsupervised hierarchal clustering of measured circulating biomarkers. Biomarkers in close correlation with each other are located close to each other, as indicated by the dendrogram at the left and the top of the graph. Positive associations are shown in red, negative associations are shown in blue and the intensity of the color represents the degree of association as quantified be Kendall's tau.

Based on the lipoprotein retention hypothesis, the retention of atherogenic, apoprotein B (apoB)-containing lipoproteins in the arterial sub-intimal layer is one of the key, initiating steps in atherosclerosis. Accordingly, serum measurements assessing the overall burden of atherogenic, apoB-containing particles have been the mainstay of cardiovascular risk stratification and modification of cardiovascular risk. Given the historical convenience of measuring low density lipoprotein (LDL) cholesterol (LDL-C) levels, measuring and monitoring LDL-C level remains the focal point of clinical guidelines of cardiovascular risk assessment and of primary and secondary prevention of atherosclerotic coronary artery disease (ASCAD).

However, in addition to lipoprotein retention, it is well-known that inflammation, endothelial dysfunction and other factors are also associated with atherosclerosis, but the cause-consequence sequence is less well established. Furthermore, LDL particles also carry triglycerides (TG) in addition to cholesterol and the functional role of TG-rich LDL particles is poorly understood.

Without wishing to be bound by theory, the present inventors have identified biomarker associations from a large suite of conventional biomarker measurements, ranked and prioritized them in an unbiased fashion based on their strength of association with atherosclerosis. An unbiased, hypothesis-free, causal, Bayesian network models were also built around those molecules that were strong, independent predictors of atherosclerosis. Furthermore, the top molecules identified were characterized as central, causally-linked factors in atherosclerosis.

This current study design provided a unique opportunity to assess biomarker associations of atherosclerosis by having completed one of the most precise and detailed quantitative phenotyping measurements of human coronary arterial atherosclerosis in a prospectively collected study using comprehensive cardiac CT analyzed in a central core laboratory, and by measuring and ranking nearly 100 circulating biomarkers.

LDL particles are the most abundant lipoprotein in the circulation and are composed of an amphipathic outer shell and an apolar inner core. The outer shell contains a phospholipid monolayer, mostly phosphatidylcholine and sphingomyelin, as well as a single molecule of apoproteinB-100 (apoB100). The apolar core contains cholesteryl esters, triglycerides and some free cholesterol, and can transition between a liquid state and a crystal phase, depending on temperature and on the triglyceride/cholesteryl ester ratio. Higher TG content is associated with the core remaining in the fluid phase, and such LDL particles have lower affinity for the LDL receptor. Therefore, higher TG content is associated with decreased clearance and longer residence time in the circulation, and TG-rich LDL particles are more readily hydrolyzed by hepatic lipase to generate small, dense LDL particles, which are considered more atherogenic than the larger particles.

Methods of Predicting

Also provided herein are methods of predicting the likelihood of the presence of cardiovascular disease and the risk of cardiovascular disease in a human subject that include: determining the level of LDL-TG in a biological sample (e.g., a blood sample) obtained from a subject, alone or in combination with at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA); and identifying the subject as being at risk of having cardiovascular disease if the level of the at least one analyte is elevated as compared to a control level.

In some embodiments, determining includes determining the level of LDL-TG in a biological sample (e.g., a blood sample) obtained from a subject, alone or in combination with at least two analytes selected from the group consisting of: LDL-TG, triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the two levels are elevated as compared to control level(s). In some embodiments, the subject is identified as being at risk of having cardiovascular disease if the levels of LDL-TG and the two analytes are elevated as compared to control levels.

In some embodiments, determining includes determining the levels of LDL-TG in a biological sample obtained from a subject, alone or in combination with at least three analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if the levels of LDL-TG and the three analytes are elevated as compared to control level(s).

In some embodiments, the subject is identified as being at risk of having cardiovascular disease if all three levels are elevated as compared to control levels.

In some embodiments, determining includes determining the level of LDL-TG in a biological sample obtained from a subject, alone or in combination with at least four analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if the levels of LDL-TG and the four analytes are elevated as compared to control level(s).

In some embodiments, the subject is identified as being at risk of having cardiovascular disease if all four levels are elevated as compared to control levels.

In some embodiments, determining includes determining the level of LDL-TG in a biological sample obtained from a subject, alone or in combination with at least five analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the five levels are elevated as compared to control level(s). In some embodiments, the subject is identified as being at risk of having cardiovascular disease if the levels of LDL-TG and the five analytes are elevated as compared to control levels.

In some embodiments, determining includes determining the level of LDL-TG in a biological sample obtained from a subject, alone or in combination with at least six analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the six levels are elevated as compared to control level(s). In some embodiments, the subject is identified as being at risk of having cardiovascular disease if the levels of LDL-TG and the six analytes are elevated as compared to control levels.

In some embodiments, determining includes determining the level of LDL-TG in a biological sample obtained from a subject, alone or in combination with at least seven analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the seven levels are elevated as compared to control level(s). In some embodiments, the subject is identified as being at risk of having cardiovascular disease if the levels of LDL-TG and the seven analytes are elevated as compared to control levels.

In some embodiments, determining includes determining the level of LDL-TG in a biological sample obtained from a subject, alone or in combination with at least eight analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the eight levels are elevated as compared to control level(s). In some embodiments, the subject is identified as being at risk of having cardiovascular disease if the levels of LDL-TG and the eight analytes are elevated as compared to control levels.

In some embodiments, determining includes determining the level of LDL-TG in a biological sample obtained from a subject, alone or in combination with at least nine analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the nine levels are elevated as compared to control level(s). In some embodiments, the subject is identified as being at risk of having cardiovascular disease if the levels of LDL-TG and the nine analytes are elevated as compared to control levels.

In some embodiments, determining includes determining the level of LDL-TG in a biological sample obtained from a subject, alone or in combination with at least ten analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the ten levels are elevated as compared to control level(s). In some embodiments, the subject is identified as being at risk of having cardiovascular disease if the levels of LDL-TG and the ten analytes are elevated as compared to control levels.

In some embodiments, determining includes determining the level of LDL-TG in a biological sample obtained from a subject, alone or in combination with at least eleven analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the eleven levels are elevated as compared to control level(s). In some embodiments, the subject is identified as being at risk of having cardiovascular disease if the levels of LDL-TG and the eleven analytes are elevated as compared to control levels.

In some embodiments, determining includes determining the level of LDL-TG in a biological sample obtained from a subject, alone or in combination with twelve analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as being at risk of having cardiovascular disease if at least one of the twelve levels are elevated as compared to control level(s). In some embodiments, the subject is identified as being at risk of having cardiovascular disease if the levels of LDL-TG and the twelve analytes are elevated as compared to control levels.

In some embodiments of any of the methods described herein, determining includes determining the level of at least one analyte selected from the group consisting of: triglycerides, IL-6, SDMA, apoB48, POA, sdLDL, ALP and ADMA.

In some embodiments, determining includes determining the levels of at least two analytes selected from the group consisting of: triglycerides, IL-6, SDMA, apoB48, POA, sdLDL, ALP and ADMA, and the subject is identified as being at risk of having cardiovascular disease if at least one of the two levels are elevated as compared to control level(s).

In some embodiments, the subject is identified as being at risk of having cardiovascular disease if both levels are elevated as compared to control levels.

In some embodiments, determining includes determining the levels of at least three analytes selected from the group consisting of: triglycerides, IL-6, SDMA, apoB48, POA, sdLDL, ALP and ADMA, and the subject is identified as being at risk of having cardiovascular disease if at least one of the three levels are elevated as compared to control level(s).

In some embodiments, the subject is identified as being at risk of having cardiovascular disease if all three levels are elevated as compared to control levels.

In some embodiments, determining includes determining the levels of at least four analytes selected from the group consisting of: triglycerides, IL-6, SDMA, apoB48, POA, sdLDL, ALP and ADMA, and the subject is identified as being at risk of having cardiovascular disease if at least one of the four levels are elevated as compared to control level(s).

In some embodiments, the subject is identified as being at risk of having cardiovascular disease if all four levels are elevated as compared to control levels.

In some embodiments, determining includes determining the levels of at least five analytes selected from the group consisting of: triglycerides, IL-6, SDMA, apoB48, POA, sdLDL, ALP and ADMA, and the subject is identified as being at risk of having cardiovascular disease if at least one of the five levels are elevated as compared to control level(s). In some embodiments, the subject is identified as being at risk of having cardiovascular disease if all five levels are elevated as compared to control levels. In some embodiments, determining includes determining the levels of at least six analytes selected from the group consisting of: triglycerides, IL-6, SDMA, apoB48, POA, sdLDL, ALP and ADMA, and the subject is identified as being at risk of having cardiovascular disease if at least one of the six levels are elevated as compared to control level(s). In some embodiments, the subject is identified as being at risk of having cardiovascular disease if all six levels are elevated as compared to control levels.

In some embodiments, determining includes determining the levels of at least seven analytes selected from the group consisting of: triglycerides, IL-6, SDMA, apoB48, POA, sdLDL, ALP and ADMA, and the subject is identified as being at risk of having cardiovascular disease if at least one of the seven levels are elevated as compared to control level(s). In some embodiments, the subject is identified as being at risk of having cardiovascular disease if all seven levels are elevated as compared to control levels.

In some embodiments, determining includes determining the levels of at least eight analytes selected from the group consisting of: triglycerides, IL-6, SDMA, apoB48, POA, sdLDL, ALP and ADMA, and the subject is identified as being at risk of having cardiovascular disease if at least one of the eight levels are elevated as compared to control level(s). In some embodiments, the subject is identified as being at risk of having cardiovascular disease if all eight levels are elevated as compared to control levels.

In some embodiments of any of the methods described herein, POA is POA (16:1n7).

Examples of single analytes or combinations of analytes that can be determined (i.e. the level determined) in a biological sample (e.g., a blood sample) in any of the methods described herein are shown in Table 1.

TABLE 1

| Examples of Single Analyte and Combination of Analytes | |
| --- | --- |
| LDL-TG, IL-6, SDMA, apoB48, POA, sdLDL, ALP and ADMA | LDL-TG and IL-6 |
| LDL-TG, IL-6, SDMA, apoB48, POA, sdLDL and ALP | LDL-TG and SDMA |
| LDL-TG, IL-6, SDMA, apoB48, POA, and sdLDL | LDL-TG and apoB48 |
| LDL-TG, IL-6, SDMA, apoB48, and POA | LDL-TG and POA |
| LDL-TG, IL-6, SDMA and apoB48 | LDL-TG and sdLDL |
| LDL-TG, IL-6 and SDMA | LDL-TG and ALP |
| LDL-TG, IL-6, SDMA and apoB48, | LDL-TG and ADMA |
| LDL-TG, IL-6 and SDMA | LDL-TG and triglycerides |
| LDL-TG, IL-6, SDMA, total cholesterol, LDL-cholesterol, HDL-cholesterol, apoB, SDMA, apoB48, POA, sd-LDL, ALP and ADMA | LDL-TG and total cholesterol |
| LDL-TG, IL-6, SDMA, total cholesterol, LDL-cholesterol, HDL-cholesterol, apoB, apoB48, POA, sd-LDL and ALP | LDL-TG and LDL-cholesterol |
| LDL-TG, IL-6, SDMA, total cholesterol, LDL-cholesterol, HDL-cholesterol, apoB, apoB48, POA and sd-LDL | LDL-TG and HDL-cholesterol |
| LDL-TG, IL-6, SDMA, total cholesterol, LDL-cholesterol, HDL-cholesterol, apoB, apoB48 and POA | LDL-TG, triglycerides, IL-6, SDMA, total cholesterol, LDL-cholesterol, HDL-cholesterol, apoB, SDMA, apoB48, POA, sd-LDL, ALP and ADMA |
| LDL-TG, IL-6, SDMA, total cholesterol, LDL-cholesterol, HDL-cholesterol, apoB and apoB48 | LDL-TG, triglycerides, IL-6, SDMA, total cholesterol, LDL-cholesterol, HDL-cholesterol, apoB, apoB48, POA, sd-LDL and ALP |
| LDL-TG, IL-6, SDMA, total cholesterol, LDL-cholesterol, HDL-cholesterol and apoB | LDL-TG, triglycerides, IL-6, SDMA, total cholesterol, LDL-cholesterol, HDL-cholesterol, apoB, apoB48, POA and sd-LDL |
| LDL-TG, IL-6, total cholesterol, LDL-cholesterol, HDL-cholesterol and apoB | LDL-TG, triglycerides, IL-6, SDMA, total cholesterol, LDL-cholesterol, HDL-cholesterol, apoB, apoB48 and POA |
| LDL-TG, total cholesterol, LDL-cholesterol, HDL-cholesterol and apoB | LDL-TG, triglycerides, IL-6, SDMA, total cholesterol, LDL-cholesterol, HDL-cholesterol, apoB and apoB |
| LDL-TG, total cholesterol, LDL-cholesterol and HDL-cholesterol | LDL-TG, triglycerides, IL-6, total cholesterol, LDL-cholesterol, HDL-cholesterol and apoB |
| LDL-TG, total cholesterol and LDL-cholesterol | LDL-TG, triglycerides, total cholesterol, LDL-cholesterol, HDL-cholesterol and apoB |
| LDL-TG, apoB48, SDMA, total cholesterol, LDL-cholesterol, HDL-cholesterol, apoB, SDMA, POA, sd-LDL, ALP and ADMA | LDL-TG, POA, apoB48, SDMA, total cholesterol, LDL-cholesterol, HDL-cholesterol, apoB, SDMA, sd-LDL, ALP and ADMA |
| LDL-TG, apoB48, SDMA, total cholesterol, LDL-cholesterol, HDL-cholesterol, apoB, SDMA, POA, sd-LDL and ALP | LDL-TG, POA, apoB48, SDMA, total cholesterol, LDL-cholesterol, HDL-cholesterol, apoB, SDMA, sd-LDL and ALP |
| LDL-TG, apoB48, SDMA, total cholesterol, LDL-cholesterol, HDL-cholesterol, apoB, SDMA, POA and sd-LDL | LDL-TG, POA, apoB48, SDMA, total cholesterol, LDL-cholesterol, HDL-cholesterol, apoB, SDMA and sd-LDL |
| LDL-TG, apoB48, SDMA, total cholesterol, LDL-cholesterol, HDL-cholesterol, apoB and SDMA | LDL-TG, POA, apoB48, SDMA, total cholesterol, LDL-cholesterol, HDL-cholesterol, apoB and SDMA |
| LDL-TG, apoB48, SDMA, total cholesterol, LDL-cholesterol, HDL-cholesterol and apoB | LDL-TG, SDMA, total cholesterol, LDL-cholesterol, HDL-cholesterol and apoB |
| LDL-TG, apoB48, SDMA, total cholesterol, LDL-cholesterol and HDL-cholesterol | LDL-TG, SDMA, total cholesterol, LDL-cholesterol and HDL-cholesterol |

TABLE 1-continued

Examples of Single Analyte and Combination of Analytes

| | |
|---|---|
| LDL-TG, apoB48, SDMA, total cholesterol and LDL-cholesterol | LDL-TG, SDMA, total cholesterol and LDL-cholesterol |
| LDL-TG, apoB48, SDMA, total cholesterol and LDL-cholesterol | LDL-TG, SDMA, total cholesterol and LDL-cholesterol |
| LDL-TG, apoB48, SDMA and total cholesterol | LDL-TG, SDMA and total cholesterol |
| LDL-TG, apoB48 and SDMA | LDL-TG and total cholesterol |
| LDL-TG and LDL-cholesterol | LDL-TG and HDL-cholesterol |
| LDL-TG, IL-6 and total cholesterol | LDL-TG, IL-6, SDMA, apoB48 and total cholesterol |
| LDL-TG, IL-6 and HDL-cholesterol | LDL-TG, IL-6, SDMA, apoB48 and LDL-cholesterol |
| LDL-TG, IL-6 and LDL-cholesterol | LDL-TG, IL-6, SDMA, apoB48 and HDL-cholesterol |
| LDL-TG, IL-6, SDMA, apoB48, POA and HDL-cholesterol | LDL-TG, IL-6, SDMA, apoB48 and POA |
| LDL-TG, IL-6, SDMA, apoB48, POA and LDL-cholesterol | LDL-TG, IL-6, SDMA, apoB48, POA and total cholesterol |
| LDL-TG, triglycerides, total cholesterol, LDL-cholesterol and HDL-cholesterol | LDL-TG, triglycerides, POA, apoB48, SDMA, total cholesterol, LDL-cholesterol, HDL-cholesterol, apoB, SDMA, sd-LDL, ALP and ADMA |
| LDL-TG, triglycerides, total cholesterol and LDL-cholesterol | LDL-TG, triglycerides, POA, apoB48, SDMA, total cholesterol, LDL-cholesterol, HDL-cholesterol, apoB, SDMA, sd-LDL and ALP |
| LDL-TG, triglycerides, apoB48, SDMA, total cholesterol, LDL-cholesterol, HDL-cholesterol, apoB, SDMA, POA, sd-LDL, ALP and ADMA | LDL-TG, triglycerides, POA, apoB48, SDMA, total cholesterol, LDL-cholesterol, HDL-cholesterol, apoB, SDMA and sd-LDL |
| LDL-TG, triglycerides, apoB48, SDMA, total cholesterol, LDL-cholesterol, HDL-cholesterol, apoB, SDMA, POA, sd-LDL and ALP | LDL-TG, triglycerides, POA, apoB48, SDMA, total cholesterol, LDL-cholesterol, HDL-cholesterol, apoB and SDMA |
| LDL-TG, triglycerides, apoB48, SDMA, total cholesterol, LDL-cholesterol, HDL-cholesterol, apoB, SDMA, POA and sd-LDL | LDL-TG, triglycerides, SDMA, total cholesterol, LDL-cholesterol, HDL-cholesterol and apoB |
| LDL-TG | |

Methods of Determining

The term "determining the amount of each analyte" as used herein refers to determining at least one characteristic feature of at least one metabolite comprised by the sample referred to herein. Characteristic features in accordance with the present invention are features which characterize the physical and/or chemical properties including biochemical properties of a metabolite. Such properties include, e.g., molecular weight, viscosity, density, electrical charge, spin, optical activity, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a metabolite by standard operations, e.g., mathematical calculations such as multiplication, division, gradient boosting, generalized linear modeling, or logarithmic calculus. Most preferably, the at least one characteristic feature allows the determination and/or chemical identification of the said at least one metabolite.

The analytes comprised by a biological sample may be determined in accordance with the present invention quantitatively or qualitatively. For qualitative determination, the presence or absence of the metabolite will be determined by a suitable technique. Moreover, qualitative determination may, preferably, include determination of the chemical structure or composition of the metabolite. For quantitative determination, either the precise amount of the analyte(s) present in the biological sample will be determined or the relative amount of the analyte(s) will be determined, preferably, based on the value determined for the characteristic feature(s) referred to herein above. The relative amount may be determined in a case were the precise amount of a metabolite can or shall not be determined. In said case, it can be determined whether the amount in which the analyte(s) is present is increased or decreased with respect to a second sample comprising said analyte(s) in a second amount. Quantitatively analyzing an analyte(s), thus, also includes what is sometimes referred to as semi-quantitative analysis of a metabolite.

Typically, the analyte level is determined by measuring the level of the metabolite in a body fluid (clinical sample), e.g., blood, serum, plasma, or urine. The level can be determined by, for example, mass spectrometry (MS), ELISA, immunoassays, enzymatic assays, spectrophotometry, colorimetry, fluorometry, bacterial assays, compound separation techniques, or other known techniques for determining the presence and/or quantity of an analyte. Separation of LDL particles may occur through precipitation methods, ultracentrifugation, electrophoresis, etc.

Compound separation techniques yield a time resolved separation of the analytes comprised by the sample. Suitable techniques for separation to be used include, for example, all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art. In some embodiments, the methods utilize LC and/or GC chromatographic techniques including, for example, gas chromatography mass spectrometry (GC-MS), liquid chromatography mass spectrometry (LC-MS), liquid chromatography-tandem mass spectrometry (UPLC-MS/MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). In some embodiments, LC-MS and/or GC-MS. As an alternative or in addition to mass spectrometry techniques, the following techniques may be used for compound determination: nuclear magnetic resonance (NMR), magnetic resonance imaging (MRI), Fourier transform infrared analysis (FT-IR), ultra violet (UV) spectroscopy, refraction index (RI), fluorescent detection, radiochemical detection, electrochemical detection, light scattering (LS), dispersive Raman spectroscopy or flame ionization detection (FID). These techniques are well known to the person skilled in the art and can be applied without further ado. In some embodiments, the methods disclosed herein shall be, optionally, assisted by automation. For example sample processing or pre-treatment can be automated by robotics. Data processing and comparison can be assisted by suitable computer programs and databases. Automation as described herein allows using the method of the present invention in high-throughput approaches.

"Determining" methods include, for example, sending a clinical sample(s) to a commercial laboratory for measurement or the use of commercially available assay kits. Commercially available assay kits are known in the art. For example, Quest Diagnostics, Sigma Aldrich, CATACHEM Inc., Eton Bioscience Inc., and Bio Vision Research Products are exemplary suppliers of such assays. Exemplary kits and suppliers will be apparent to the skilled artisan.

In some cases, the methods disclosed herein involve comparing levels to a reference. The reference can take on a variety of forms. In some cases, the reference comprises predetermined values for the analytes (e.g., each of analytes). The predetermined value can take a variety of forms. It can be a level of an analyte obtained from a subject known to have cardiovascular disease, or obtained from a subject known not to suffer from cardiovascular disease (e.g., a healthy subject). It can be a level of an analyte obtained from a subject having no previous history of cardiovascular disease. It can be a level in the same subject, e.g., at a different time point.

A predetermined value that represents a level(s) of an analyte is referred to herein as a predetermined level. A predetermined level can be single cut-off value, such as a median or mean. It can be a range of cut-off (or threshold) values, such as a confidence interval. It can be established based upon comparative groups, such as where the risk in one defined group is a fold higher, or lower, (e.g., approximately 2-fold, 4-fold, 8-fold, 16-fold or more) than the risk in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

Moreover, the reference could be a calculated reference, most preferably the average, mean or median, for the relative or absolute amount of an analyte of a population of individuals comprising the subject to be investigated. The absolute or relative amounts of the analytes of the individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 subjects. It is to be understood that the subject to be diagnosed by the method of the present invention and the subjects of the said plurality of subjects are of the same species.

Subjects associated with predetermined values are typically referred to as control subjects (or controls). A control subject does not have cardiovascular disease. In some cases it may be desirable that control subject is a symptomatic subject, and in other cases it may be desirable that a control subject is an asymptomatic subject. In other cases the level of an analyte in a subject being less than or equal to the level of the analyte in a control subject is indicative of a clinical status.

The predetermined value can depend upon a particular population of subjects (e.g., human subjects) selected. For example, an apparently healthy population will have a different 'normal' range of metabolites than will a population of subjects which have, or are likely to have, cardiovascular disease. Accordingly, the predetermined values selected may take into account the category (e.g., healthy, at risk, diseased, age, gender, etc.) in which a subject (e.g., human subject) falls. Appropriate ranges and categories can be selected with no more than routine experimentation by those of ordinary skill in the art. In some cases a predetermined value of an analyte (e.g., a biomarker) is a value that is the average for a population of healthy subjects (human subjects) (e.g., human subjects who have no apparent signs and symptoms of cardiovascular disease). The predetermined value will depend, of course, on the particular analyte selected and even upon the characteristics of the population in which the subject lies. In characterizing likelihood, or risk, numerous predetermined values can be established. The predetermined values may be obtained from subjects in whom the presence or absence of cardiovascular disease was determined by a reference standard method ("gold standard method"). In some embodiments, the reference standard method may be cardiac CT imaging.

A level, in some embodiments, may itself be a relative level that reflects a comparison of levels between two states. Relative levels that reflect a comparison (e.g., ratio, difference, logarithmic difference, percentage change, etc.) between two states (e.g., healthy and diseased) may be referred to as delta values. The use of relative levels is beneficial in some cases because, to an extent, they exclude measurement related variations (e.g., laboratory personnel, laboratories, measurements devices, reagent lots/preparations, assay kits, etc.). However, the invention is not so limited.

Kits

Also provided herein are kits that include any of the reagents suitable for determining levels of the at least one analyte in a biological sample obtained from a subject, wherein the at least one analyte is selected from the group consisting of: total cholesterol, LDL-cholesterol, HDL-cholesterol, triglycerides, apoB, IL-6, SDMA, apoB48, POA, sd-LDL, ALP and ADMA. In some embodiments, the kits can include instructions for performing any of the methods described herein. In some embodiments, the reagents suitable for determining levels of the at least one analyte are disposed in a multi-well plate (e.g., a 96-well plate or a 384-well plate). In some embodiments of any of the kits described herein, the kit includes a multi-well plate (e.g., a 96-well plate or a 384-well plate). In some embodiments of any of the kits described herein, the kit includes one or more control samples (e.g., a negative reference sample and/or a positive reference sample).

EXAMPLES

The invention is further described in the following examples, which do not limit the scope of the invention described in the claims.

Example 1. Case/Control Analysis within the Genetic Loci and the Burden of Atherosclerotic Lesions Study ("GLOBAL" Study, NCT01738828)—Study Design The overall design of the GLOBAL study has been published in detail (Voros et al. J Cardiovasc Comput Tomogr. 2014 November-December; 8(6):442-51.). Briefly, the GLOBAL study recruited over 7,500 subjects referred for cardiovascular computed tomography (CT) for suspected atherosclerotic coronary artery disease (CAD). A total of 48 clinical sites participated in the study. The study was performed based on the principles of Good Clinical Practices. The Electronic Data Capture system was compliant with CFR Part 21 requirements. All patients provided written, informed consent. The GLOBAL study protocol was approved by all relevant Institutional Review Boards and/or Ethics Committees. Data from the source documentation was entered into an Electronic Data Capture system by local study personnel and the data was 100% monitored by independent study personnel. The study was sponsored and funded by Global Genomics Group, LLC.

The study was a priori designed based on the Institute of Medicine and American Heart Association guidelines for biomarker discovery and validation (Hlatky et al., Circulation 2009; 119(17):2408e2416.). The designation of a "Case" was defined based on the presence of any coronary atherosclerotic plaque, as detected by cardiovascular CT, using combined interpretation of non-contrast-enhanced and contrast-enhanced CT scans. Subjects with no discernible atherosclerotic plaque on non-contrast enhanced CT and no discernible plaque on the contrast CT angiogram (CTA) were classified as "Controls". Subjects with any discernible plaque on either the non-contrast CT or the contrast-enhanced CTA were classified as "Cases".

Laboratory Methods

A total of 99 blood-based biomarkers were measured at a large subspecialty reference laboratory using commercial kits, reagents and protocols, as shown in Table 2. Serum and plasma samples were stored at −80° prior to analysis. Low Density Lipoprotein Triglycerides (LDL-TG) measurements were performed by a two-step process using protocols by Denka Seiken. Lipoproteins other than LDL were decomposed in the first step and triglycerides from the remaining LDL particles were quantified by enzymatic reactions in the second step. In the first step we applied a specific surfactant (surfactant 1) and cholesterol esterase to decompose non-LDL lipoprotein particles. Triglycerides that originated from such non-LDL lipoprotein particles were finally degraded to water and oxygen through reactions with lipoprotein lipase, glycerol kinase, L-α-glycerophosphate oxidase and catalase. In the second step, triglycerides from LDL particles were determined by measuring the purple-red color that was developed under the presence of another surfactant (surfactant 2) and peroxidase.

TABLE 2

List of Biomarkers Measured

| Abbreviation | Full Name | Units | Manufacturer/Method |
|---|---|---|---|
| AA2 | Arachidonic acid | % | HDL Gas Chromatography |
| AAEPA | Arachidonic divided by EPA | % | HDL Gas Chromatography |
| ADMA | Asymmetric dimethylarginine | ng/mL | HDL Mass Spec. |
| ADMA.Arg.Ratio | Asymmetric dimethylarginine/arginine ratio | | HDL Mass Spec. |
| ADN | Adiponectin | μg/mL | MedTest |
| ALB | Albumin | g/dL | Beckman Coulter |
| ALP | Alkaline phosphatase | U/L | Beckman Coulter |
| alphalin2 | Alpha-linoleic acid | % | HDL Gas Chromatography |
| ALT | Alanine transaminase | U/L | Beckman Coulter |
| APO.A1 | Apolipoprotein A-I | mg/dL | Beckman Coulter |
| APO.B | Apolipoprotein B | mg/dL | Beckman Coulter |
| ApoB48 | APO Protein B48 | ng/mL | Shibayagi |
| arachidic2 | Arachidic acid | % | HDL Gas Chromatography |
| AST | Aspartate transaminase | U/L | Beckman Coulter |
| B.Sitosterol | B-Sitosterol | μg/ml | In-house Mass Spec. |
| behenic2 | Behenic acid | % | HDL Gas Chromatography |
| C.PEP | C-Peptide | ng/mL | Roche |
| CALA | Calcium | mg/dL | Beckman Coulter |
| Campesterol | Campesterol | μg/ml | In-house Mass Spec. |

TABLE 2-continued

List of Biomarkers Measured

| Abbreviation | Full Name | Units | Manufacturer/Method |
|---|---|---|---|
| CHOL | Total Cholesterol | mg/dL | Beckman Coulter |
| Cholestanol | Cholestanol | µg/ml | In-house Mass Spec. |
| cismontotl | Palmitoleic + oleic + eicosenoic + nervonic | % | HDL Gas Chromatography |
| CK8 | Cytokeratin-8 | ng/mL | HDL ELISA |
| CRE | Creatinine | mg/dL | Beckman Coulter |
| DBILC | Direct Bilrubin | mg/dL | Beckman Coulter |
| dcopentn32 | Docosapentaenoic-n3 acid | % | HDL Gas Chromatography |
| dcopentn62 | Docosapentaenoic-n6 acid | % | HDL Gas Chromatography |
| Desmosterol | Desmosterol | µg/ml | In-house Mass Spec. |
| DHA2 | Docosahexaenoic acid | % | HDL Gas Chromatography |
| dihomolin2 | Dihomolinoleic acid | % | HDL Gas Chromatography |
| docosat2 | Docosatetraenoic acid | % | HDL Gas Chromatography |
| eicosad2 | Eicosadienoic acid | % | HDL Gas Chromatography |
| eicosen2 | Eicosenoic acid | % | HDL Gas Chromatography |
| EPA2 | Eicosapentaenoic acid | % | HDL Gas Chromatography |
| Fibrinogen | Fibrinogen | mg/dL | Kamiya |
| Folate | Serum Folate | ng/mL | Roche |
| Galectin3 | Galectin 3 | ng/mL | BG Medicine |
| gammalin2 | Gamma linoleic acid | % | HDL Gas Chromatography |
| GGT | Gamma-glutamyl transferase | U/L | Beckman Coulter |
| GLU | Glucose | mg/dL | Beckman Coulter |
| GPF | Gamma Prime Fibrinogen | mg/dL | Gamma Therapeutic |
| HbA1C | Glycated hemoglobin A1C | % | Trinity Biotech. |
| HCY | Homocysteine | µmol/L | Diazyme |
| HDL.APOE | APO E Mass on HDL | mg/dL | Denka |
| HDL.C | High Density lipoprotein Cholesterol | mg/dL | Randox (Denka reagent) |
| HDL3.C | High Density Lipoprotein Fraction 3 Cholesterol | mg/dL | Randox (Denka reagent) |
| hs.cTnI | High Sensitivity Cardiac Tropin-I | pg/mL | Quanterix |
| hsCRP | High Sensitive C Reactive Protein | mg/L | Beckman Coulter |
| IL17A.Ran | Interleukin-17A | pg/mL | Randox |
| IL17A.Sim | Interleukin-17A | pg/mL | Simoa |
| IL-6 | Interleukin-6 | pg/mL | Randox |
| Insulin | Insulin | µU/mL | Roche |
| LDH | Lactate dehydrogenase | U/L | Beckman Coulter |
| LDL.TG | LDL Triglycerides | mg/dL | Denka |
| LDL.C | Low Density Lipoprotein Cholesterol | mg/dL | Beckman Coulter |
| Leptin | Leptin | ng/mL | Mercodia |
| ligno2 | Lignoceric acid | % | HDL Gas Chromatography |
| linoleic2 | Linoleic acid | % | HDL Gas Chromatography |
| Lpa.ApoA.Size | Size of ApoA in Lp(a) | | |
| Lpa.ApoB.percent | ApoB in Lp(a) | % | |
| Lpa.C.Elect | Lipoprotein (a) cholesterol | mg/dL | Electrophoresis |
| Lpa.Mass | Lipoprotein (a) Mass | mg/dL | Randox (reagent made by Denka) |
| Lpa.P.Elect | Lipoprotein (a) Particle by Electrophoresis | nmol/L | Electrophoresis |
| Lpa.P.ELISA | Lipoprotein (a) Particle by ELISA | nmol/L | Sun Diagnostics |
| LpPLA2.ACT | Lipoprotein Associated Phospolipase A2 Activity | U/L | Diazyme |
| LpPLA2.Mass.DDX | Lipoprotein Associated Phospolipase A2 Mass | ng/mL | DiaDexus |

TABLE 2-continued

List of Biomarkers Measured

| Abbreviation | Full Name | Units | Manufacturer/ Method |
|---|---|---|---|
| LpPLA2.Mass ITA | Lipoprotein Associated Phospolipase A2 Mass | ng/mL | Denka immuno-turbidmetric assay |
| MMA | Methylmalonic acid | μmol/L | HDL Mass Spec. |
| MPO | Myeloperoxidase | pmol/L | Cleveland Heart Lab |
| myristic2 | Myristic acid | % | HDL Gas Chromatography |
| NEFA | Non-esterified fatty acids | mmol/L | Wako |
| nervonic2 | Nervonic acid | % | HDL Gas Chromatography |
| NTProBNP | N-terminal pro-brain natriuretic peptide | pg/mL | Roche |
| O3Index | Omega 3 index | % | HDL Gas Chromatography |
| O3total | Omega 3 total | % | HDL Gas Chromatography |
| O6O3 | O6 total divided by O3 total | % | HDL Gas Chromatography |
| O6total | Omega 6 total | % | HDL Gas Chromatography |
| OCN | Osteocalcin | ng/mL | Roche |
| oleic2 | Oleic acid | % | HDL Gas Chromatography |
| OxLDL | Oxidized LDL (mass) | U/mL | Corgenix |
| palmitic2 | Palmitic acid | % | HDL Gas Chromatography |
| palmleic2 | Palmitoleic acid | % | HDL Gas Chromatography |
| PCSK9 | Proprotein convertase subtilisin/kexin type 9 | ng/mL | RnD system |
| PHOS | Phosphorous | mg/dL | Beckman Coulter |
| ProInsulin | ProInsulin | pmol/L | Mercodia |
| PTH | Parathyroid hormone | pg/mL | Roche |
| RBP4 | Retinol Binding Protein 4 | mg/L | Diazyme |
| RLP | Remnant Lipoproteins Cholesterol | mg/dL | Denka |
| sattotal | Total saturated fatty acids | % | HDL Gas Chromatography |
| sdLDL.C.AU5840 | Small Dense Low Density Lipoprotein Cholesterol | mg/dL | Denka, AU5840 analyzer |
| sdLDL.C.P.Mod | Small Dense Low Density Lipoprotein Cholesterol | mg/dL | Denka, Roche P Modular analyzer |
| SDMA | Symmetric dimethylarginine | ng/mL | HDL Mass Spec. |
| stearic2 | Stearic acid | % | HDL Gas Chromatography |
| TBILC | Total Bilirubin | mg/dL | Beckman Coulter |
| TNFA.Ran | Tumor Necrosis Factor Alpha | pg/mL | Randox |
| TNFA.Sim | Tumor Necrosis Factor Alpha | pg/mL | Simoa |
| tomegaprct | Total omega percent | % | HDL Gas Chromatography |
| TP | Total Protein | g/dL | Beckman Coulter |
| translin2 | Translinoleic acid | % | HDL Gas Chromatography |
| transol2 | Transoleic acid | % | HDL Gas Chromatography |
| transpalm2 | Transpalmitoleic acid | % | HDL Gas Chromatography |
| transtotal | Trans palmitoleic + trans oleic + trans linoleic | % | HDL Gas Chromatography |
| TRIG | Triglycerides | mg/dL | Beckman Coulter |
| UA | Uric Acid | mg/dL | Beckman Coulter |
| VEGF | Vascular Endothelial Growth Factor | pg/mL | Randox |
| VIT.B12 | Vitamin B12 | pg/mL | Roche |
| VIT.D | Vitamin D | ng/mL | Diasorin |

Cardiovascular Computed Tomography (CT) Image Acquisition

Cardiovascular CT image acquisition was performed at each participating clinical site based on the sites' institutional protocols for cardiovascular CT with imaging acquisition guidelines provided by the sponsor. Participation in the GLOBAL study required a 64-slice scanner system or higher. Patients enrolled in the GLOBAL study underwent non-contrast CT for the quantification of coronary artery calcium (CAC), followed by contrast-enhanced coronary CT angiogram (CTA).

Cardiovascular CT Image Analysis

All images were transferred to a central image analysis core laboratory (Global Institute for Research, Richmond, Va.) using AG Mednet for image transfer, and the Vital Enterprise System (Vital Images; Minnetonka, Minn.) for image storage and analysis. Non-contrast CAC scans were analyzed for the amount of coronary artery calcium by using the Agatston score as well as the volume score, on a per-patient and per-vessel basis. For qualitative analysis, coronary arterial segmentation was performed based on a modified 17-segment model, as suggested by the Society for Cardiovascular Computed Tomography (Raff et al., J Cardiovasc Computed Tomography 2009; 3:122e136); each segment was graded for plaque type, degree of stenosis, plaque features and plaque pattern. Plaque was classified as none, non-calcified plaque (NCP), partially calcified plaque (PCP) or calcified plaque (CAP). Stenosis was graded as none, minimal (<25%), mild (25-49%), moderate (50-69%), severe (70-99%) or occluded (100%), based on percent diameter stenosis. Plaque features were assessed as proposed by Motoyama et al., based on the presence of positive remodeling, low attenuation plaque, or both (Motoyama et al., J Am Coll Cardiol. 2007; 50(4):319e326.). Plaque pattern was assessed as suggested by Maurovich-Horvat; non-calcified components of NCP and PCP were graded as homogenous, heterogeneous, or having a napkin ring sign (NRS) (Maurovich-Horvat et al., JACC Cardiovasc Imaging. 2012; 5(12):1243e1252). In addition to segmental analysis, composite, patient-level scores were also calculated, including the segment involvement score (SIS), based on the number of segments with any plaque, segment stenosis score (SSS), obtained by summing all stenosis scores in all segments, and the composite coronary score (CCS), which was calculated by summing the product of the plaque and stenosis score within each segment. Finally, the SIS, SSS and CCS were normalized by multiplying each score by the number of segments present in a given patient, divided by 17, yielding SISi, SSSi and CCSi.

Isolation of Genomic DNA

Isolation of Genomic DNA using the QIAamp® DNA Blood Midi Kit (Qiagen part no. 51185). Starting from 0.3 to 1 ml of whole blood, a lysis buffer and protease are added to each sample for cell lysis. After lysis, the lysate is loaded onto a QIAamp® spin column. DNA binds to the QIAamp® membrane while impurities are washed away in two vacuum steps. Upon drying the membrane, DNA is eluted in 200 µl of elution buffer. The yield of genomic DNA is subsequently determined by PicoGreen® quantitation or by using the Qubit® fluorometer.

Whole Genome Sequencing (Illumina® Service Laboratory)

Illumina® FastTrack Whole Human Genome Sequencing (WGS) Service was powered by the HiSeq® 2000 System, providing a high-quality genome at a minimum of 30×average coverage. The following paragraphs briefly describe the general methodologies employed by FastTrack WGS to construct and sequence DNA libraries and generate WGS data. These descriptions include methodologies for TruSeq® DNA PCR-free library construction, TruSeq® Sequencing by Synthesis (SBS) v3 chemistry, and the Infinium® HumanOmni2.5-8 genotyping array.

Genomic DNA (gDNA) Quantitation

Genomic DNA was quantified prior to library construction using PicoGreen® (Quant-iT™ PicoGreen® dsDNA Reagent, Invitrogen™, Catalog #: P11496). Quants were read with Spectromax Gemini™ XPS (Molecular Devices).

Library Construction—Polymerase Chain Reaction (PCR)-Free

Paired-end libraries were manually generated from 500 ng-1 ug of gDNA using the Illumina® TruSeq® DNA Sample Preparation Kit (Catalog #: FC-121-2001), based on the protocol in the TruSeq® DNA PCR-Free Sample Preparation Guide. Pre-fragmentation gDNA cleanup was performed using paramagnetic sample purification beads (Agencourt® AMPure® XP reagents, Beckman Coulter). Samples were fragmented and libraries were size selected following fragmentation and end-repair using paramagnetic sample purification beads, targeting 300 base pair (bp) inserts. Final libraries were quality controlled for size using a gel electrophoretic separation system and were quantified.

Clustering and Sequencing—v3 Chemistry

Following library quantitation, DNA libraries were denatured, diluted, and clustered onto v3 flow cells using the Illumina® cBot™ system. cBot™ runs were performed based on the cBot™ User Guide, using the reagents provided in Illumina® TruSeq® Cluster Kit v3. Clustered v3 flow cells were loaded onto HiSeq™ 2000 instruments and sequenced on 100 bp paired-end, non-indexed runs. All samples were sequenced on independent lanes. Sequencing runs were performed based on the HiSeq™ 2000 User Guide, using Illumina® TruSeq® SBS Kit v3 Reagents. Illumina® HiSeq™ Control Software (HCS) and Real-Time Analysis (RTA) was used on HiSeq™ 2000 sequencing runs for real-time image analysis and base calling.

Genotyping

Samples were processed using Infinium® chemistry, based on the Infinium® LCG Assay Guide, and run on the HumanOmni2.5-8 array. Resulting intensity .idat files were loaded into GenomeStudio® software (http://www.illumina.com/software/genomestudio_software.ilmn) to export genotyping calls.

RNA Isolation from PAXgene® Blood miRNA Kit

RNA isolation was completed using the PAXgene® Blood miRNA Kit (Qiagen, Venlo, Netherlands). PAXgene® Blood RNA Tubes were first centrifuged to pellet the samples, then washed with water and resuspended. After digestion with proteinase K, the samples were homogenized by centrifugation through PAXgene® Shredder spin columns. Isopropanol was added to the samples to optimize binding conditions, and the samples were then centrifuged through PAXgene® RNA spin columns, where total RNA>18 nucleotides (including miRNA) was bound to the silica-membrane. The bound RNA was treated with DNase to remove genomic DNA contamination and washed. Pure RNA was then eluted.

Small RNA Sequencing Methods and Materials

Libraries were prepared for small RNA sequencing using the TruSeq® Small RNA Sample Prep Kit (Illumina®). Prior to library preparation, RNA samples were quantitated by spectrophotometry using a Nanodrop™ ND-8000 spectrophotometer, and assessed for RNA integrity using an Agilent 2100 BioAnalyzer or Caliper LabChip® GX. RNA samples with A260/A280 ratios ranging from 1.6-2.2, with RNA integrity number (RIN) values ≥7.0, and for which at least 1000 ng of total RNA was available proceeded to library preparation. Total RNA samples were prepared using extraction chemistry that did not exclude small RNA species, for example, the QIAGEN miRNeasy kit.

Library preparation began with 1000 ng of total RNA in 5 µl of nuclease-free water, to which an adapter oligonucleotide was added. Next, the adapter oligonucleotide was ligated to the 3' hydroxyl present on miRNA species using T4 RNA Ligase (New England Biolabs). Similarly, a different adapter sequence was ligated to the 5' end of RNAs that possessed a 5' phosphate, to create a single-stranded molecule with defined sequences at both the 5' and 3' ends. This molecule was reverse-transcribed and amplified using 14 cycles of PCR using primers that included sequences complementary to the 5' and 3' adapter sequences, a specific index sequence, and Illumina® sequencing adapter sequences. The resulting product was analyzed using an Agilent 2100 BioAnalyzer and the molar amount of mature miRNA present in the library was estimated by integrating the area under the curve in the 145-160 bp range. Individual libraries were mixed to create multiplexed pools, and the mixture was purified by gel electrophoresis, wherein the 145-160 bp range was excised from the gel, crushed using a Gel Breaker tube (IST Engineering), eluted into nuclease-free water, and concentrated by precipitation with ethanol. The concentration of the final library pool was determined using PicoGreen® (Invitrogen™) and the size distribution of the pool was determined using an Agilent 2100 BioAnalyzer. Library pools were normalized to 2 nM in preparation for sequencing.

TruSeq® Stranded mRNA Sequencing

Prior to library preparation, alpha and beta globin mRNA was reduced using the GLOBINclear™-Human Kit (Life Technologies, Carlsbad, Calif.) following the manufacturers protocol. Total RNA samples were converted into cDNA libraries using the TruSeq® Stranded mRNA Sample Prep Kit (Illumina®, #RS-122-2103). Starting with 100 ng of total RNA, polyadenylated RNA (primarily mRNA) was selected and purified using oligo-dT conjugated magnetic beads. This mRNA was chemically fragmented and converted into single-stranded cDNA using reverse transcriptase and random hexamer primers, with the addition of actinomycin D to suppress DNA-dependent synthesis of the second strand. Double-stranded cDNA was created by removing the RNA template and synthesizing the second strand in the presence of dUTP in place of dTTP. A single A base was added to the 3' end to facilitate ligation of sequencing adapters, which contain a single T base overhang. Adapter-ligated cDNA was amplified by polymerase chain reaction to increase the amount of sequence-ready library. During this amplification the polymerase stalled when it encountered a U base, rendering the second strand a poor template. Accordingly, amplified material used the first strand as a template, thereby preserving the strand information. Final cDNA libraries were analyzed for size distribution and using an Agilent Bioanalyzer (DNA 1000 kit, Agilent #5067-1504), quantitated by qPCR (KAPA Library Quant Kit, KAPA Biosystems # KK4824), then normalized to 2 nM in preparation for sequencing.

Mass-Spectrometry-Based Proteomics Methods

Proteomic discovery experiments were performed in two stages. The first stage was performed using non-targeted mass spectrometry, and the second stage of targeted mass spectrometry was performed using multiple reaction monitoring (MRM).

Discovery Experiments Using Non-Targeted Mass Spectrometry

Plasma samples from 338 subjects (corresponding to 169 pairs of control and index subjects) were randomized to avoid introducing bias in the analysis. Samples were processed essentially as described previously (Li et al., Sci Transl Med 2013, 5(207): p. 207ra142). Briefly, each 30 µL sample was depleted of high abundance proteins using an affinity resin (IgY14/Seppro® Supermix, Sigma). All columns were prepared with the same manufacturing batch of affinity resin and tested for consistent performance prior to use. Control samples, consisting of aliquots of a pooled human plasma sample, were inserted at the start, middle and end of each set of 20 paired study samples, resulting in a batch size of 23. After depletion, samples were frozen, freeze-dried, digested with trypsin (1:10, w:w, Promega®) and desalted on Empore™ C18 plates (3M Bioanalytical Technologies). Resulting peptides were separated by strong cation exchange (SCX, Waters) chromatography into six fractions with a linear salt gradient and desalted on Oasis® HLB plates (Waters). Samples were distributed into two 96-well plates (one test plate and one back-up plate). Samples were dried and resuspended in 96.25/3.75 (v/v) water/acetonitrile and 0.1% formic acid, containing 19 internal standard peptides. Mass spectrometry analysis was performed by nanoflow reversed phase liquid chromatography (nanoAcquity UPLC, Waters®) coupled by electrospray (Michrom ADVANCE™ CaptiveSpray™ MS Source) to a high resolution mass spectrometer (Q Exactive™ Thermo-Scientific) in LC-MS and LC-MS/MS mode. The LC column was used at a flow rate of 1.8 µL/min (Waters® nanoAcquity UPLC® column BEH130 C18, 150 µm×100 mm, 1.7 µm). Each of the six fractions were run as a separate set of 338 samples plus control samples.

Intensity data files for each LC-MS run within a SCX fraction was aligned using Elucidator® (Rosetta Biosoftware). Peak intensities for each peptide ion were extracted across all files. LC-MS/MS files were analyzed by Mascot (Matrix Sciences) and the Uniprot human protein database (version 2013_08) to assign high confidence peptide sequences to the observed peptide ions. All sequenced peptides were then clustered by their parent proteins. Potential intensity bias introduced by sample processing and/or loss of sensitivity of the mass spectrometer over the time of the experiment was corrected by normalization. The normalization procedure was based on a regression model predicting log-intensity level on a per-peptide basis. First, the mean raw log-intensity for each peptide was calculated. Then the regression model (linear regression or natural cubic spline smoothing) for sample processing variables was fit to the data. Finally, the normalized log-intensity was computed as the raw log-intensity minus the regression-predicted log-intensity plus the mean raw log-intensity.

The statistical significance of the intensity differences between the various clinical groups was assessed using a paired t-test, performed independently on each peptide and each protein, for the matched atherosclerosis and control samples. An ANOVA model was also used to compare the same two groups to account for dyslipidemia, hypertension and diabetes status covariates, which were not matched between sample pairs. All statistical test p-values were adjusted for multiple testing by conversion to q-value using Storey's method.

Metabolomics and Lipidomics Methods by Mass Spectrometry

Samples were stored at −70° C. until processed. Recovery standards were added prior to the first step in the extraction process for quality control purposes. To remove protein, dissociate small molecules bound to protein or trapped in the precipitated protein matrix, and to recover chemically diverse metabolites, proteins were precipitated with methanol under vigorous shaking for 2 min (Glen Mills Geno/Grinder® 2000) followed by centrifugation. The resulting extract was divided into four fractions: one for analysis by ultra-high performance liquid chromatography-tandem mass spectrometry (UPLC-MS/MS; positive mode), one for analysis by UPLC-MS/MS (negative mode), one for analysis by gas chromatography-mass spectrometry (GC-MS), and one sample was reserved for backup.

Three types of controls were analyzed in concert with the experimental samples: samples generated from a pool of human plasma (extensively characterized by Metabolon, Inc.) served as technical replicate throughout the data set;

extracted water samples served as process blanks; and a cocktail of standards spiked into every analyzed sample allowed instrument performance monitoring. Instrument variability was determined by calculating the median relative standard deviation (RSD) for the standards that were added to each sample prior to injection into the mass spectrometers (median RSD=5%; n=30 standards). Overall process variability was determined by calculating the median RSD for all endogenous metabolites (i.e., non-instrument standards) present in 100% of the pooled human plasma samples (median RSD=11%; n=610 metabolites). Experimental samples and controls were randomized across the platform run.

Non-targeted MS analysis was performed at Metabolon, Inc. Extracts were subjected to either GC-MS or UPLC-MS/MS. The chromatography was standardized and, once the method was validated no further changes were made. As part of Metabolon's general practice, all columns were purchased from a single manufacturer's lot at the outset of experiments. All solvents were similarly purchased in bulk from a single manufacturer's lot in sufficient quantity to complete all related experiments. For each sample, vacuum-dried samples were dissolved in injection solvent containing eight or more injection standards at fixed concentrations, depending on the platform. The internal standards were used both to assure injection and chromatographic consistency. Instruments were tuned and calibrated for mass resolution and mass accuracy daily.

The UPLC-MS/MS platform utilized a Waters® Acquity UPLC® with Waters® UPLC® BEH C18-2.1×100 mm, 1.7 μm columns and a Thermo Scientific Q-Exactive™ high resolution/accurate mass spectrometer interfaced with a heated electrospray ionization (HESI-II) source and Orbitrap™ mass analyzer operated at 35,000 mass resolution. The sample extract was dried then reconstituted in acidic or basic LC-compatible solvents, each of which contained 8 or more injection standards at fixed concentrations to ensure injection and chromatographic consistency. One aliquot was analyzed using acidic, positive ion-optimized conditions and the other using basic, negative ion-optimized conditions in two independent injections using separate dedicated columns. Extracts reconstituted in acidic conditions were gradient eluted using water and methanol containing 0.1% formic acid, while the basic extracts, which also used water/methanol, contained 6.5 mM ammonium bicarbonate. The MS analysis alternated between MS and data-dependent $MS^2$ scans using dynamic exclusion, and the scan range was from 80-1000 m/z.

The samples destined for analysis by GC-MS were dried under vacuum desiccation for a minimum of 18 h prior to being derivatized under dried nitrogen using bistrimethylsilyltrifluoroacetamide. Derivatized samples were separated on a 5% phenyldimethyl silicone column with helium as carrier gas and a temperature ramp from 60° to 340° C. within a 17-min period. All samples were analyzed on a Thermo-Finnigan™ Trace™ DSQ™ MS operated at unit mass resolving power with electron impact ionization and a 50-750 atomic mass unit scan range.

Compound Identification, Quantification, and Data Curation

Metabolites were identified by automated comparison of the ion features in the experimental samples to a reference library of chemical standard entries that included retention time, molecular weight (m/z), preferred adducts, and in-source fragments as well as associated MS spectra and curated by visual inspection for quality control using software developed at Metabolon. Identification of known chemical entities was based on comparison to metabolomic library entries of purified standards. Over 2,500 commercially available purified standard compounds have been acquired and registered into LIMS for distribution to both the LC/MS and GC/MS platforms for determination of their detectable characteristics. An additional 250 mass spectral entries have been created for structurally unnamed biochemicals, which have been identified by virtue of their recurrent nature (both chromatographic and mass spectral). These compounds have the potential to be identified by future acquisition of a matching purified standard or by classical structural analysis. Peaks were quantified using area-under-the-curve. Raw area counts for each metabolite in each sample were normalized to correct for variation resulting from instrument inter-day tuning differences by the median value for each run-day, therefore, setting the medians to 1.0 for each run. This preserved variation between samples but allowed metabolites of widely different raw peak areas to be compared on a similar graphical scale. Missing values were imputed with the observed minimum after normalization.

TrueMass® Lipomic Panel

Lipids were extracted in the presence of authentic internal standards using chloroform:methanol (2:1 v/v). For the separation of neutral lipid classes [free fatty acid (FFA), triacylglycerol (TAG), diacylglycerol (DAG), cholesteryl ester (CE)], a solvent system consisting of petroleum ether/diethyl ether/acetic acid (80:20:1) was employed. Individual phospholipid classes within each extract [phosphatidylcholine (PC), phosphatidylethanolamine (PE)] were separated using the Agilent Technologies 1100 Series LC. Each lipid class was transesterified in 1% sulfuric acid in methanol in a sealed vial under a nitrogen atmosphere at 100° C. for 45 minutes. The resulting fatty acid methyl esters were extracted from the mixture with hexane containing 0.05% butylated hydroxytoluene and prepared for GC by sealing the hexane extracts under nitrogen. Fatty acid methyl esters were separated and quantified by capillary GC (Agilent Technologies 6890 Series GC) equipped with a 30 m DB 88 capillary column (Agilent Technologies) and a flame ionization detector.

Statistical Analysis

Univariate associations were assessed against several quantitative phenotype measurements of coronary artery plaque, stenosis and disease burden and were displayed as a "heatmap" with a dendrogram using hierarchal clustering, based on Kendal's tau values. Gradient boosting was performed from fifty starting points (seeds) to determine the most consistent set of predictors; their relative influence was plotted. Association of LDL-TG with atherosclerosis was assessed by odds ratios with 95% confidence intervals. Normally distributed continuous variables are expressed as mean±SD; non-normally distributed continuous variables are expressed as median [inter-quartile range (IQR)]. Since LDL-TG exhibited skewed distribution, natural log transformation (Log(1+x)) was applied. Statistical significance was placed at a p-value of 0.05 or less.

Bayesian Network Analysis: Reverse Engineering with Forward Simulation (REFS™)

Whole genome sequencing, DNA methylation analysis of approximately 450,000 sites, and quantification of ~28,000 mRNA's and ~6,000 micro-RNA's from circulating mononuclear cells, ~1,800 proteins, ~800 metabolites and ~150 complex lipid species was performed.

In order to investigate the set of causal relationships among the 99 measured biomarkers, tens of thousands "omics" measurements, and atherosclerotic Case/Control status, an ensemble of 256 Bayesian networks was learned using a Monte-Carlo Bayesian causal machine learning platform, REFS™ (Reverse Engineering with Forward Simulation). By construction, Bayesian networks are enriched for causal relationships among variables; REFS learns hypothesis-free causal networks from biological data and estimates model uncertainty by sampling multiple models from the Bayesian posterior distribution of models. This approach minimized the risk of overfitting and, through ensemble frequency, allowed for identification of the key causal relationships that were consistently important.

Demographic Features and Atherosclerosis in the Patient Population

A total of 665 subjects were included in the study. General demographic features are shown in Table 3. Chest pain and atypical angina were present in 63% and 36%, respectively. In general, mean age in the overall study population was 56±11, 47% were male and mean Diamond-Forrester score was 26% (range 0-94%). Low-density lipoprotein cholesterol (LDL-C), high-density lipoprotein cholesterol (HDL-C) and triglycerides in "Cases" and "Controls" are also shown in Table 3. Prevalence of atherosclerosis ("Case") was 52% in the overall cohort. Seven percent of patients had zero coronary artery calcium score but had non-calcified plaque. Predominantly non-calcified, partially calcified and calcified plaque were present in 7%, 36% and 57% of cases, respectively. Napkin ring sign, a high-risk feature by CT, was seen in 10% of patients. Moderate stenosis (50-69%) was the highest degree of stenosis in 7% subjects and 16% had moderate-to-severe stenosis (50% or greater luminal stenosis). Mean SIS and SISi were 2.2±3.1 and 2.4±3.3%, respectively.

TABLE 3

General Demographic Features of Subjects

| | Controls N = 348 | Atherosclerosis N = 317 | p-value |
|---|---|---|---|
| Age (years) | 54.2 | 57.6 | <0.001 |
| Male N; (%) | 141 (44.5) | 171 (49.1) | NS |
| Diamond-Forrester Score (mean, SE) | 23.0 (1.6) | 28.5 (1.7) | NS |
| LDL-C; mg/dL; (mean, SE) | 115.7 (2.0) | 111.7 (1.9) | NS |
| ApoB; mg/dL; (mean, SE) | 91.3 (1.4) | 91.2 (1.4) | NS |
| HDL-C; mg/dL; (mean, SE) | 56.9 (0.9) | 58.9 (1.0) | NS |
| Triglycerides; mg/dL (mean, SE) | 150.1 (5.2) | 176.5 (8.1) | NS |
| LDL-TG; mg/dL (mean, SE) | 17.2 (0.4) | 19.5 (0.7) | <0.001 |
| Hypertension N; (%) | 162 (51.3) | 249 (72.0) | <0.001 |
| Type II Diabetes N; (%) | 23 (7.3) | 60 (17.2) | <0.001 |
| Statin use N; (%) | 105 (33.1) | 200 (57.5) | <0.001 |
| Niacin use N; (%) | 5 (1.6) | 5 (1.4) | NS |
| Fibrate use N; (%) | 18 (5.2) | 12 (3.8) | NS |
| Ezetimibe use N; (%) | 6 (1.9) | 18 (5.2) | NS |
| Fish oil use N; (%) | 27 (8.5) | 51 (14.7) | NS |
| Bile Acid Sequestrant use N; (%) | 3 (1.0) | 1 (0.3) | NS |

Example 2. Biomarker Associations with Atherosclerosis

Of the 99 biomarkers measured, 25 biomarkers had significant associations with at least one other biomarker (raw p<0.05) as shown in FIG. 1. Based on unsupervised hierarchal clustering, there were 4 major groups of biomarkers. Cluster 1 included ApoB-containing lipoprotein particle related measurements, including LDL-TG; Cluster 2 included measures of insulin resistance, diabetes and fatty acids; Cluster 3 included measures of endothelial dysfunction, inflammation and fibrosis and Cluster 4 included measures of intestinal cholesterol absorption and vitamin-D.

Figure 2:
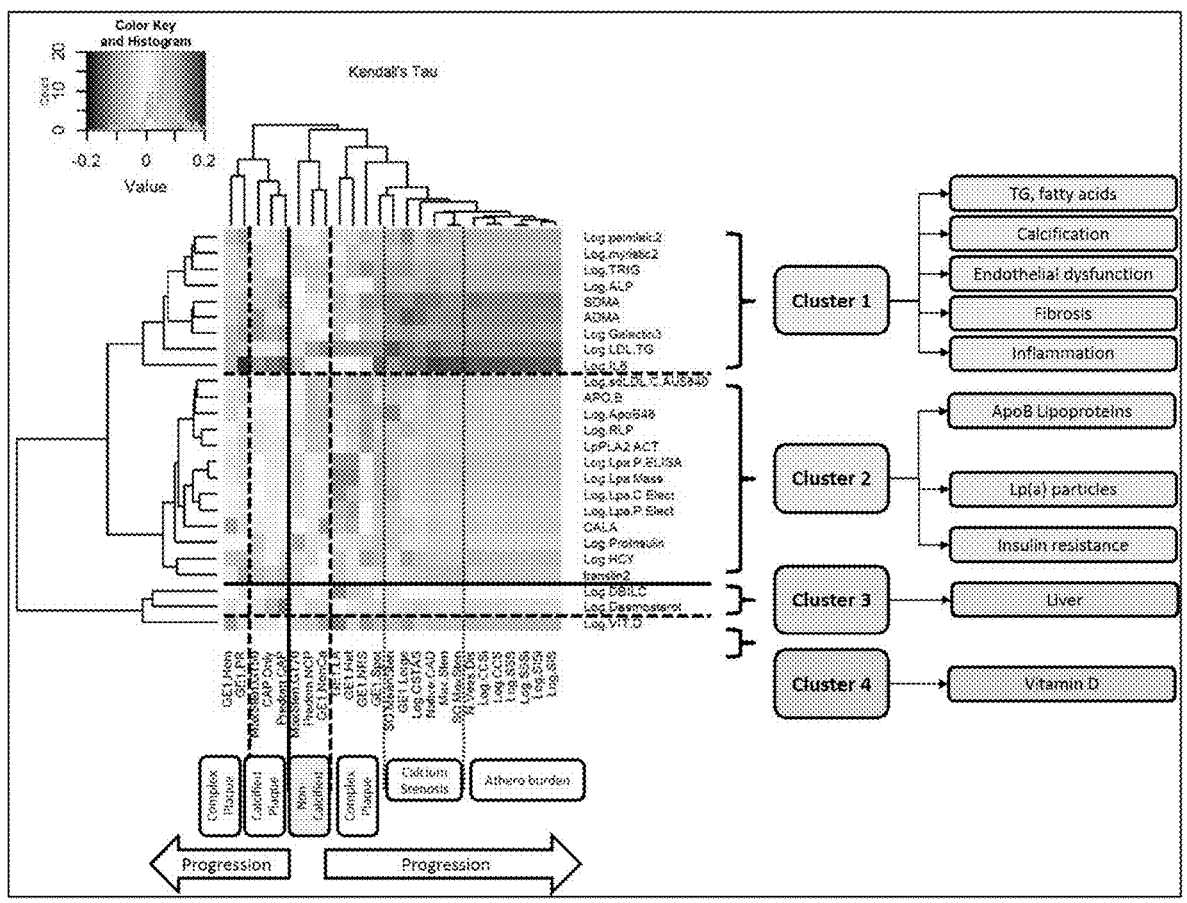
FIG. 2 is an exemplary clustogram showing the results of an unsupervised clustering of circulating biomarkers against quantitative measures of atherosclerotic plaque, stenosis and coronary artery disease burden. Each row represents a biomarker with significant association with at least one CT-measurement of atherosclerosis and each column represents a CT-measurement of atherosclerosis. The dendrogram on the left represents associations between circulating biomarkers and the dendrogram on the top represents the degree of association between quantitative measures of atherosclerosis. Positive associations are shown in red, negative associations are shown in blue and the intensity of the color represents the degree of association as quantified be Kendall's tau

30 biomarkers had significant univariate association (raw p<0.05) with at least one measure of atherosclerosis as shown in the "heatmap" with the dendrogram in FIG. 2. 8 were selected by gradient boosting (interleukin-6 (IL-6), symmetric dimethylarginine (SDMA), LDL-triglycerides (LDL-TG), apolipoprotein B48 (apoB48), palmitoleic acid (POA), small dense LDL (sd-LDL), alkaline phosphatase (ALP) and asymmetric dimethylarginine (ADMA). As shown in FIG. 2, there are 6 major clusters of CT-measurements of atherosclerosis: non-calcified plaque, complex plaque, calcification/stenosis, disease burden, calcified plaque and a second cluster of complex plaque. There are 4 distinct clusters of circulating biomarkers with different patterns of association with different measures of atherosclerosis. Cluster 1 included triglycerides, including LDL-TG, fatty acids and measures of endothelial dysfunction, inflammation and fibrosis. Cluster 2 included ApoB-containing lipoprotein measurements, Lp(a) and measures of insulin resistance. Cluster 3 included hepatic measurements and a marker of cholesterol synthesis, and Cluster 4 had vitamin-D alone.

Figure 3:
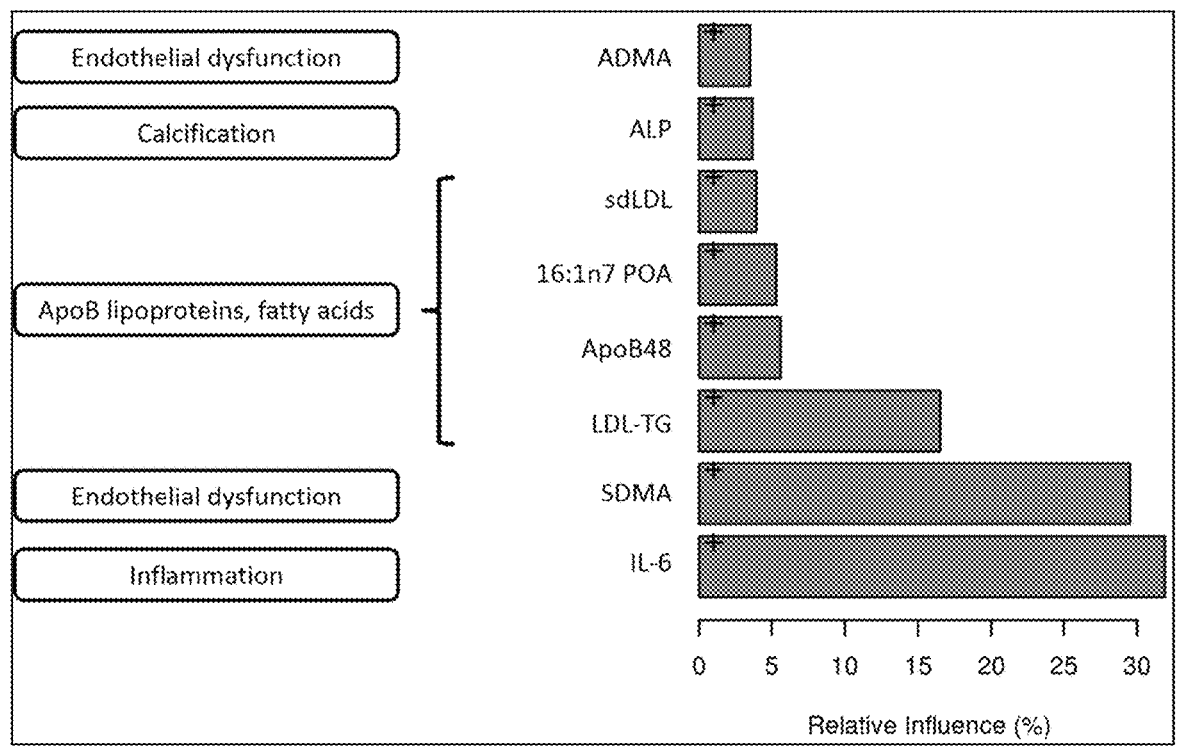
FIG. 3 is an exemplary bar graph showing the top 8 biomarkers that are independently associated with atherosclerotic coronary artery disease. The length of the bar graphs indicates the relative influence of each of the 8 biomarkers in predicting the presence of atherosclerotic coronary artery disease.

Biomarkers that had a significant univariate association with Case/Control status were subjected to multiple seed gradient boosting analysis to identify those with independent predictive value; those biomarkers that were significantly associated with Case/Control status are shown in FIG. 3, indicating their relative influence in the prediction of the presence of absence of atherosclerosis. Importantly, out of the 99 biomarkers measured, IL-6, symmetric dimethylarginine (SDMA) and LDL-TG were the top 3, independent predictors of Case/Control status with a relative influence over ~30% for IL-6 and SDMA and ~15% for LDL-TG.

In the context of increased triglyceride levels, cholesteryl ester transfer protein (CETP) preferentially moved TG from VLDL through IDL to LDL particles, while CE were moved from LDL through IDL to VLDL particles. TG-rich LDL particles were cleared less efficiently through the LDL receptor and could be hydrolyzed by lipases to form sd-LDL. Markers of endogenous, hepatic synthesis of fatty acids (myristic acid, 14:0; palmitate, 16:0 and its derivative, palmitoleic acid (POA), 16:1n7) were elevated in subjects with atherosclerosis and were localized in the same cluster as LDL-TG (FIG. 2). POA (16:1n7) was an independent predictor in the multi-variable analysis (FIG. 3). In addition, apoB48, a carrier and marker of intestinal TG and cholesterol, was also an independent predictor of atherosclerosis on multi-variable analysis (FIG. 3). Markers of inflammation (IL-6, CRP, fibrinogen and LpPLA2), fibrosis (galectin-3) and endothelial dysfunction (ADMA and SDMA) were also seen on univariate, multi-variable and Bayesian network analysis. In Bayesian network analysis, markers of fatty acid synthesis (myristic acid; 14:0 palmitate; 16:0 and its derivative, palmitoleic acid (POA); 16:1n7) and intestinal TG uptake (apoB48) were upstream from LDL-TG, while markers of inflammation, endothelial dysfunction and fibrosis were downstream.

Example 3. LDL-TG and Atherosclerosis

Figure 4:
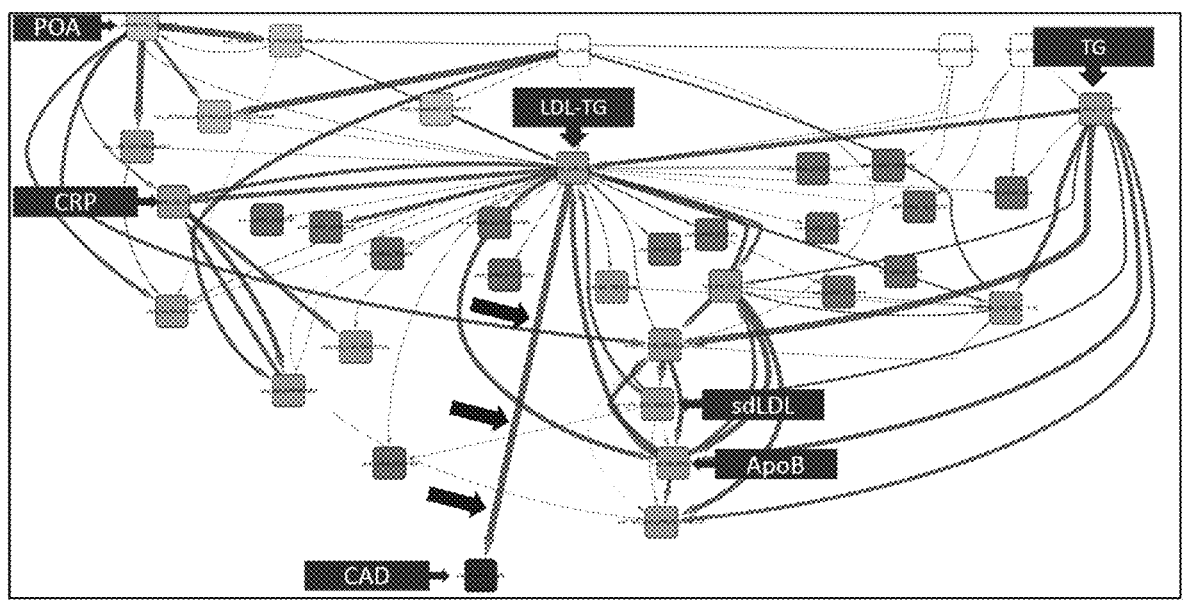
FIG. 4 is an output from an exemplary hypothesis-free Bayesian network analysis using reverse engineering with forward simulation (REFS™) showing the subnetwork of measurements with one degree of separation from LDL-TG. Arrow thickness indicates the fraction of networks in which the causal edge appears; different color boxes represent different types of measurements (yellow: mass-spect-based lipidomics; pink: mass-spect-based metabolomics; green: gene expression (mRNA); grey: conventional biomarker measurements).

The primary result and output from unbiased Bayesian network analysis is shown in FIG. 4. The ensemble of Bayesian networks identified from the data consisted of 24,929 nodes and 110,350 edges occurring in more than 5% of models in the ensemble. The results, indicated that LDL-TG was the only biomarker directly upstream from the presence of atherosclerotic CAD, occurring in 95% of networks in the ensemble. This suggested a potential causal role of TG-rich LDL particles, as measured by LDL-TG's, in atherosclerosis. Given the central role of LDL-TG in the Bayesian networks, attention was focused on LDL-TG to further elucidate its potential contribution to atherosclerosis.

LDL-TG was significantly higher in native CAD vs. controls (20.19±0.93 vs. 17.21±0.40 mg/dL; p<0.001), with an odds ratio (95% confidence interval) of 3.41 (1.94-6.01). Odds ratios for atherosclerosis were analyzed in four quartiles of LDL-TG measurements. Odds ratios in the $2^{nd}$ through the $4^{th}$ quartiles were 1.38 (95% CI: 0.86-2.24), 1.43 (95% CI: 0.89-2.31) and 2.84 (95% CI: 1.75-4.64), compared to the $1^{st}$ quartile (Table 4).

By unsupervised hierarchal clustering, it was observed that ApoB-containing lipoprotein measurements clustered together, red-cell membrane-based fatty acid measurements clustered with measurements of insulin resistance and diabetes, and measurements of endothelial dysfunction, inflammation and fibrosis clustered together, indicating that they are in similar biological pathways (FIG. 1). ApoB-containing lipoproteins, insulin resistance, endothelial dysfunction, inflammation and fibrosis were strongly associated with human coronary atherosclerosis as shown by an unbiased univariate and multi-variable analyses in FIG. 2 and FIG. 3.

Figure 5A:
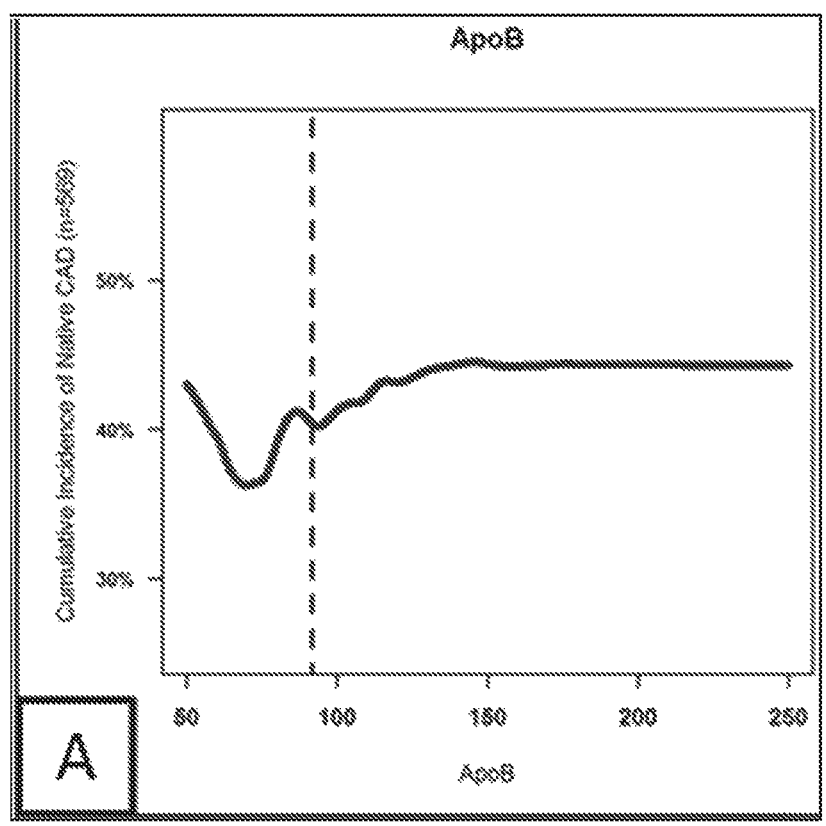
FIGS. 5A-F are cumulative incidence curves for the presence of coronary atherosclerosis as a function of ApoB, LDL-C and LDL-TG.
Figure 5B:
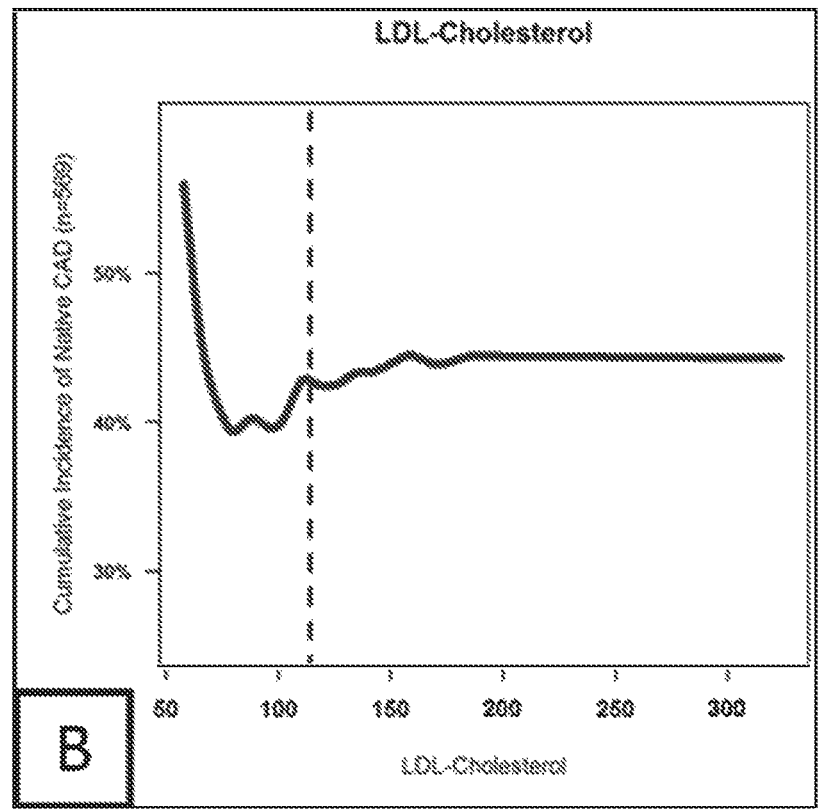
Figure 5C:
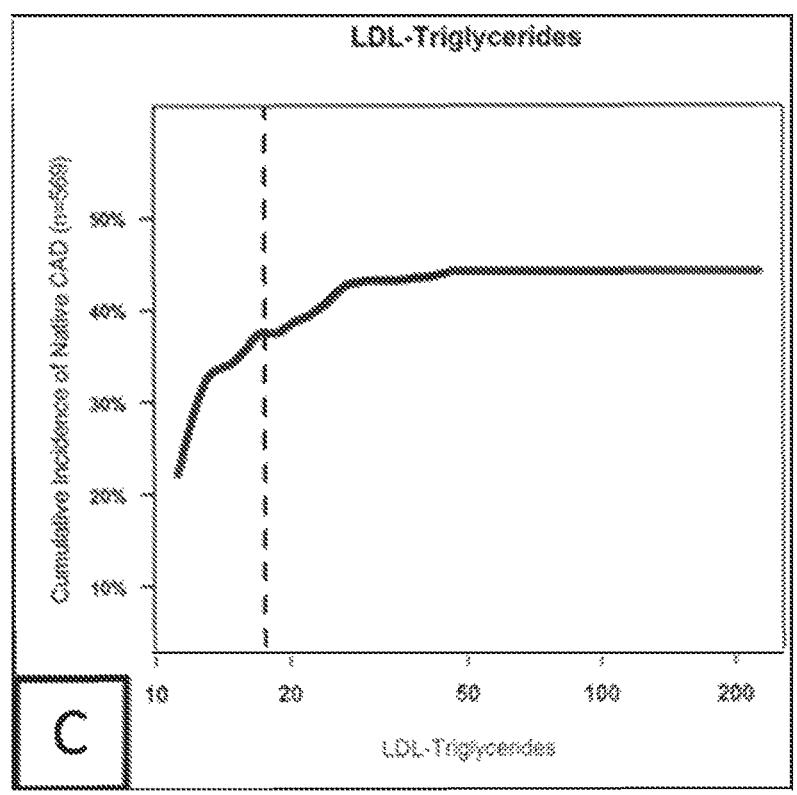
Figure 5D:
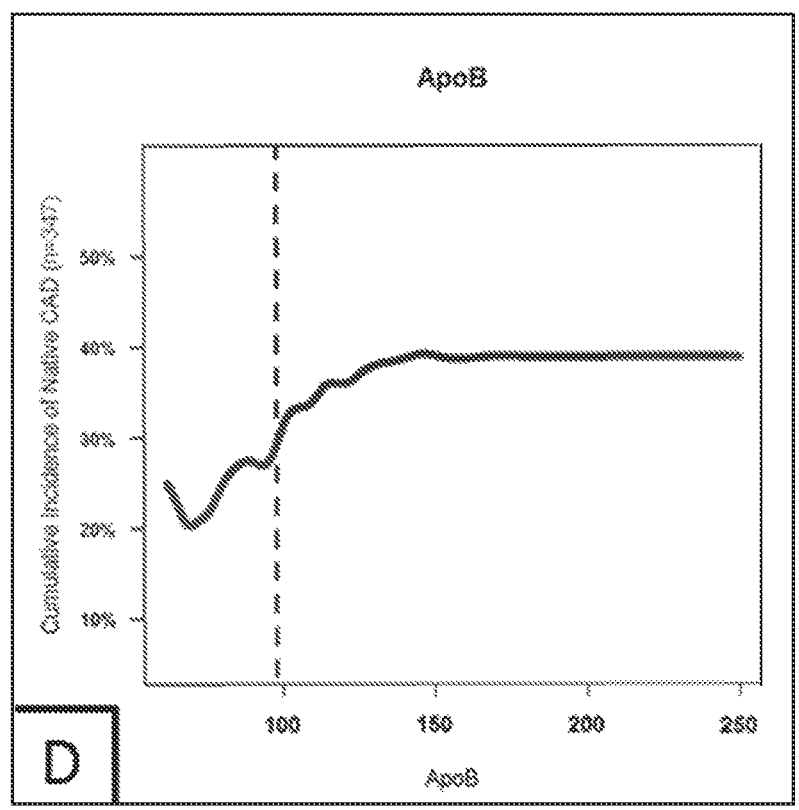
Figure 5E:
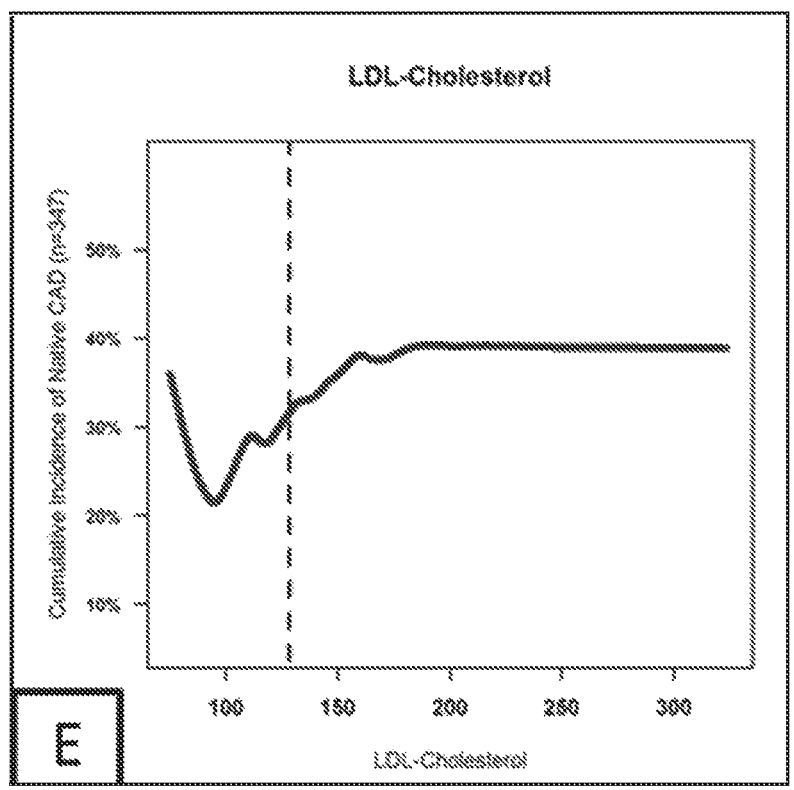

In more detailed analysis, the known "sigmoid" relationship between serum levels of LDL-C and human coronary atherosclerosis was confirmed (FIG. 5E). It is important to point out, however, that the contribution of LDL-C to atherosclerosis only explained the prevalence of atherosclerosis in the 20-40% range. While this "sigmoid" LDL-C/

TABLE 4

Odds Ratios (95% CI) for LDL-TG in Pre-Specified Models

|  | Quartile 1 | Quartile 2 | Quartile 3 | Quartile 4 | p-value against $4^{th}$ quartile | p-value for trend |
|---|---|---|---|---|---|---|
| LDL-TG Unadjusted | Reference | 1.38 (0.86, 2.24) | 1.43 (0.89, 2.31) | 2.84 (1.75, 4.64) | 2.67e−05 | 5.35e−05 |
| LDL-TG Model 1* | Reference | 1.31 (0.80, 2.13) | 1.39 (0.86, 2.27) | 3.00 (1.84, 4.95) | 1.38e−05 | 2.50e−05 |
| LDL-TG Model 2** | Reference | 1.43 (0.88, 2.33) | 1.56 (0.95, 2.56) | 3.36 (1.95, 5.85) | 1.50e−05 | 3.88e−05 |
| LDL-TG Model 3*** | Reference | 1.34 (0.82, 2.20) | 1.48 (0.89, 2.46) | 3.37 (1.94, 5.91) | 1.86e−05 | 4.49e−05 |

Figure 5F:
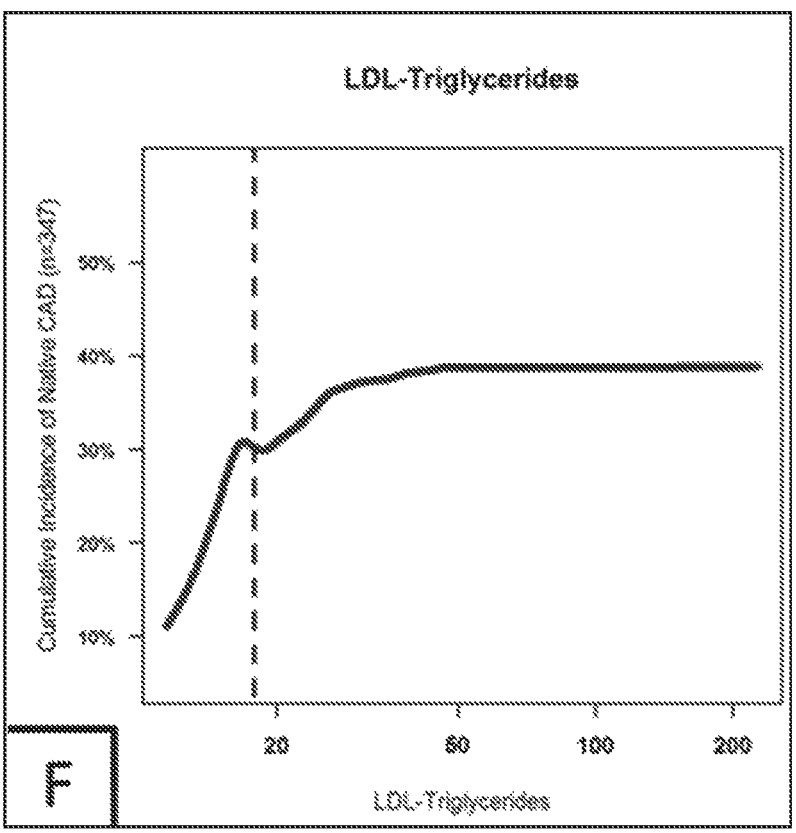

*Adjusted for age and gender
**Adjusted for LDL-C
***Adjusted for age, gender and LDL-C Example 4. Cumulative Incidence Curves To examine the relative contribution of each of the key measurements to atherosclerosis, cumulative incidence curves were constructed for ApoB, LDL-C and LDL-TG against the cumulative incidence of atherosclerosis in all subjects, and also in subjects not on statins at the time of the study visit (FIG. 5). Cumulative incidence curves (CIC) demonstrated the well-described "sigmoid" relationship between ApoB and LDL-C levels, mostly in the ApoB range of 50-150 mg/dL and in the LDL-C range of 60-200 mg/dL. The curves were significantly influenced in statin-treated patients (FIGS. 5A-B), where the cumulative incidence of atherosclerosis was high despite very low levels of ApoB (FIG. 5A) and LDL-C(FIG. 5B), likely representing patients with known CAD and aggressive statin therapy. The "sigmoid" relationship for ApoB and LDL-C was more apparent when statin-treated patients were excluded (FIGS. 5D-E). On the other hand, a clear, "sigmoid", or "near exponential" relationship was seen as a function of serum LDL-TG levels, with no apparent effect of statin therapy (FIG. C and FIG. 5F). The left tails of the CIC curves were highly influenced by patients with known CAD whose LDL-C and ApoB-levels were likely lowered by recent statin therapy, showing a high cumulative incidence of CAD at very low levels of LDL-C and ApoB. Importantly, statin therapy appeared to have little influence on the cumulative incidence of CAD as a function of LDL-TG measurements (FIG. 5 C and FIG. 5F).

CAD curve has been the foundation of LDL-C lowering to reduce cardiovascular disease morbidity and mortality, it has been underemphasized that, even if subjects had very low levels of circulating LDL-C and ApoB, the prevalence of CAD was still about 20%, indicating that other biological pathways beyond LDL particles were also responsible for the presence of CAD. On the other hand, the "sigmoid" curve completely flattened out over LDL-C levels of approximately 200 mg/dL (ApoB levels of approximately 150 mg/dL), and even in subjects with very high levels of LDL-C over this threshold, the prevalence of atherosclerosis was "only" 40%, suggesting that a large portion of the population might not have been "susceptible" to high levels of circulating ApoB-containing lipoprotein particles. In this context, LDL-TG measurements explained a wider range of the prevalence of atherosclerosis, between 10 and 40% (FIG. 5F).

Interestingly, while the left tail of the LDL-C and ApoB cumulative incidence curves were heavily influenced by patients with known CAD in whom lipid-lowering therapy was used to lower these biomarkers, LDL-TG measurements were largely independent of the effect of statin therapy, suggesting that LDL-TG measurements might be more reliable in the detection of atherosclerotic CAD in subjects on statin treatment for high LDL-C levels.

Out of 24,929 variables and 110,350 significant edges in the Bayesian network models, LDL-TG was a strong direct driver of human coronary atherosclerosis in 95% of models in the ensemble, while ApoB, LDL-C, TG, ApoA1, and HDL-C were not identified as causal drivers. It is important to emphasize that FIG. 4 was not an illustration, but the actual output of the Bayesian model built on our dataset. A total of 24,929 nodes and 110,350 edges were discovered in more than 5% of networks in the ensemble. It is striking to note that of the biomarkers measured and included in the model, LDL-TG was the only direct connection to atherosclerotic CAD (see blue arrows pointing to LDL-TG to CAD edge), suggesting that TG-rich lipoprotein particles, as measured by LDL-TG, may be the culprit, causal lipoprotein particles in atherosclerosis. In this model, TG levels and 16:1n7 POA (palmitoleic acid) were upstream from LDL-TG, while sd-LDL and inflammatory markers (CRP, fibrinogen, Lp-PLA2) were downstream from LDL-TG. Interestingly, in this causal model, sdLDL, ApoB and CRP were downstream from LDL-TG, while 16:1n6 POA and total triglyceride levels appeared upstream from LDL-TG. Fibrinogen and galectin-3 were downstream from CRP. This might be consistent with a mechanistic hypothesis where TG-rich LDL particles drive downstream inflammation, a fibrotic response and directly contribute to the initiation and progression of human coronary atherosclerotic plaques (FIG. 6).

Figure 6:
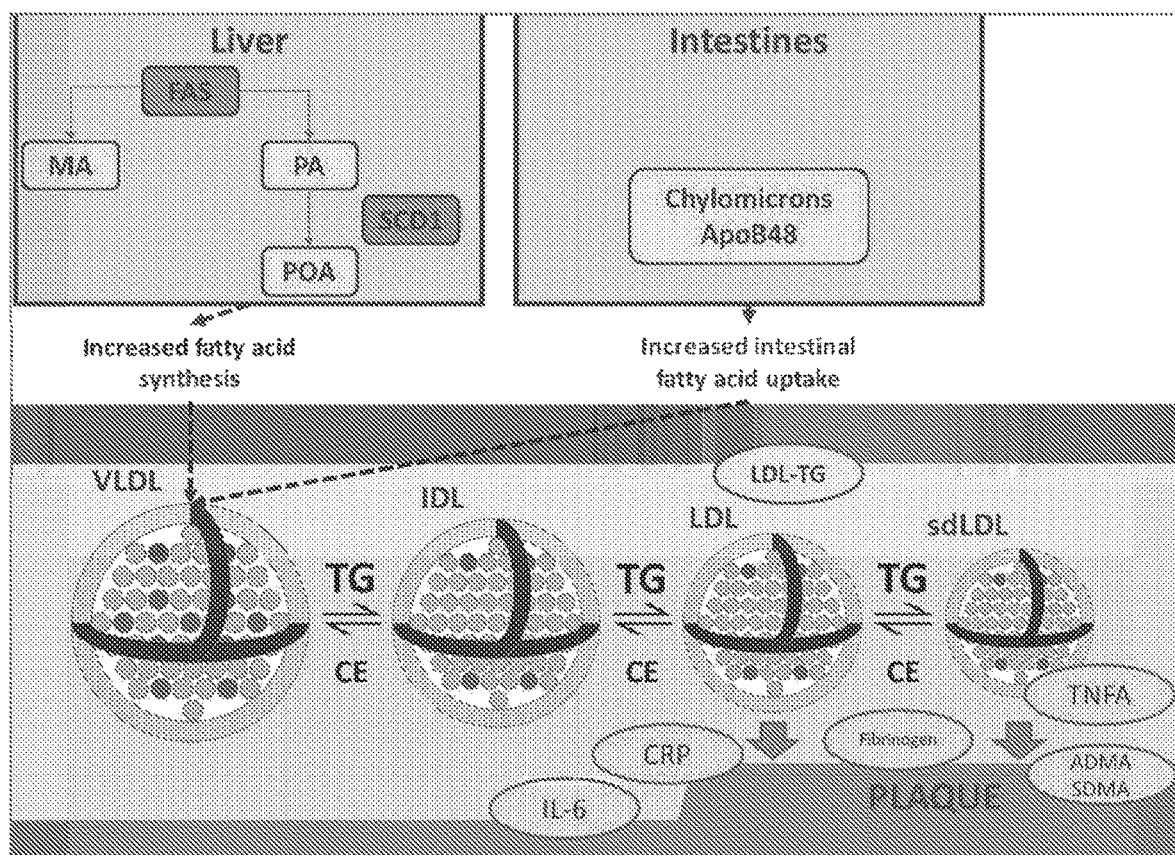
FIG. 6 is a schematic of a proposed biological pathway of the atherogenicity of triglyceride-rich LDL particles.

This data was consistent with a hypothesis where increased fatty acid load from the liver and the diet lead to increased levels of circulating TG-rich LDL particles, which led to the formation of sd-LDL particles and to a downstream inflammatory reaction and endothelial dysfunction, culminating in the initiation and propagation of atherosclerosis (FIG. 6). As shown in FIG. 6, fatty acid synthesis in the liver (indicated by myristic acid, palmitate and palmitoleic acid) and intestinal markers of intestinal cholesterol and TG uptake (apoB48) may result in increased TG load, leading to the formation of TG-rich VLDL particles. In the circulation, TG is moved through IDL to LDL particles in exchange for CE, potentially by CETP. TG-rich LDL particles, as indicated by LDL-TG measurements, have lower affinity for the LDL receptor for clearance and therefore have longer circulating residence time, making them more amenable to hydrolysis by various lipases, generating small, dense LDL particles. TG-rich LDL particles and small, dense LDL particles may trigger downstream inflammation, endothelial dysfunction and may ultimately culminate in facilitating atherosclerosis.

In summary, this was one of the most comprehensive and unbiased analyses of tens of thousands of circulating biomarkers against atherosclerosis, using quantitative, precision phenotyping by comprehensive cardiac CT. Without wishing to be bound by theory, the present inventors found that apoB-containing lipoproteins, inflammatory biomarkers, markers of endothelial dysfunction and fibrosis were associated with human coronary atherosclerosis. Importantly, based on unbiased Bayesian network analysis, TG-rich LDL particles, as measured by LDL-TG, were identified as a key and potentially causal factor in atherosclerosis. Taken together, these findings are consistent with a hypothesis where increased fatty acid load from hepatic synthesis and intestinal uptake lead to enrichment of LDL particles in TG and simultaneous depletion in CE, rendering LDL particles more resistant to clearance by the LDL receptor. TG-rich LDL particles are more readily hydrolyzed to form sd-LDL particles, and TG-rich LDL particles and sd-LDL particles trigger downstream inflammation, endothelial dysfunction and culminate in the development of atherosclerosis. With the recent introduction of a simple and reliable method for the quantification of LDL-TG, this may become an important tool in the assessment of patients at risk for, or with, atherosclerosis.

Triglyceride-rich LDL particles, as measured by LDL-TG, may play an important role in atherogenesis and may serve as an additional biomarker for risk stratification.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing atherosclerotic coronary artery disease in a human subject, the method comprising:
decomposing lipoproteins other than low density lipoproteins (LDL) from a blood sample obtained from a human subject, yielding a LDL particle sample;
measuring the level of low density lipoprotein triglycerides (LDL-TG) in the LDL particle sample;
comparing the measured level of LDL-TG in the LDL particle sample with one or more reference samples, wherein the one or more reference samples are representative of at least one individual not suffering from atherosclerotic coronary artery disease;
identifying the human subject as having atherosclerotic coronary artery disease if the level of LDL-TG in the LDL particle sample is elevated as compared to the level of LDL-TG in the one or more reference samples, and
administering a treatment for atherosclerotic coronary artery disease to the subject identified as having atherosclerotic coronary artery disease, wherein the treatment is selected from the group consisting of: a peroxisome proliferator-activated receptor (PPAR)-alpha agonist, a PPAR gamma agonist, and niacin.

2. The method of claim 1, further comprising measuring the level of at least one analyte in the blood sample obtained from the subject, wherein the at least one analyte is selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA), and identifying the subject as having atherosclerotic coronary artery disease if the levels of LDL-TG and the at least one analyte are both elevated as compared to levels of LDL-TG and the at least one analyte in the one or more reference samples.

3. The method of claim 2, wherein measuring comprises measuring the levels of at least two analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having atherosclerotic coronary artery disease if the levels of LDL-TG and at least one of the at least two analytes are elevated as compared to the levels of LDL-TG and the at least one of the at least two analytes in the one or more reference samples.

4. The method of claim 3, wherein the subject is identified as having atherosclerotic coronary artery disease if the level of LDL-TG and both levels of the at least two analytes are elevated as compared to the level of LDL-TG and both levels of the at least two analyte levels in the one or more reference samples.

5. The method of claim 2, wherein measuring comprises measuring the levels of at least three analytes selected from the group consisting of:
triglycerides, total cholesterol, LDL-cholesterol, HDL-cholesterol, apoB, IL-6, SDMA, apoB48, POA, sd-LDL, ALP and ADMA, and the subject is identified as having atherosclerotic coronary artery disease if the levels of LDL-TG and at least one of the at least three analytes are elevated as compared to the levels of LDL-TG and the at least one level of the at least three analytes in the one or more reference samples.

6. The method of claim 5, wherein the subject is identified as having atherosclerotic coronary artery disease if the levels of LDL-TG and all three of the at least three analytes are elevated as compared to the levels of LDL-TG and all three of the at least three analytes in the one or more reference samples.

7. The method of claim 2, wherein measuring comprises measuring the levels of at least four analytes selected from the group consisting of: triglycerides, total cholesterol, LDL-cholesterol, HDL-cholesterol, apoB, IL-6, SDMA, apoB48, POA, sd-LDL, ALP and ADMA, and the subject is identified as having atherosclerotic coronary artery disease if the levels of LDL-TG and at least one of the four analytes are elevated as compared to the levels of LDL-TG and the at least one of the at least four analytes in the one or more reference samples.

8. The method of claim 7, wherein the subject is identified as having atherosclerotic coronary artery disease if the levels of LDL-TG and all four of the at least four analytes are elevated as compared to the levels of LDL-TG and all four of the at least four anayltes in the one or more reference samples.

9. The method of claim 2, wherein measuring comprises measuring the level of at least one of triglycerides, IL-6, SDMA, apoB48, POA, sdLDL, ALP and ADMA.

10. The method of claim 2, wherein POA is palmitoleic acid 16:1n7.

11. A method of diagnosing atherosclerotic coronary artery disease in a human subject, the method comprising:
decomposing lipoproteins other than low density lipoproteins (LDL) from a blood sample obtained from a human subject, yielding a LDL particle sample;
measuring the level of low density lipoprotein triglycerides (LDL-TG) in the LDL particle sample;
measuring the level of at least one analyte selected from the group consisting of: triglycerides, total cholesterol, low density lipoprotein (LDL)-cholesterol, high density lipoprotein (HDL)-cholesterol, apolipoprotein B (apoB), interleukin 6 (IL-6), symmetric dimethylarginine (SDMA), apolipoprotein B48 (apoB48), palmitoleic acid (POA), small dense LDL (sd-LDL), alkaline phosphatase (ALP) and asymmetric dimethylarginine (ADMA),
comparing the measured level of LDL-TG in the LDL particle sample and the level of the at least one analyte with one or more reference samples, wherein the one or more reference samples are representative of at least one individual not suffering from atherosclerotic coronary artery disease; and
identifying the human subject as having atherosclerotic coronary artery disease if the levels of LDL-TG in the LDL particle sample and the at least one analyte are both elevated as compared to the levels of LDL-TG and the at least one analyte in the one or more reference samples, and
administering a treatment for atherosclerotic coronary artery disease to the subject identified as having atherosclerotic coronary artery disease, wherein the treatment is selected from the group consisting of: a peroxisome proliferator-activated receptor (PPAR)-LDL, alpha agonist, a PPAR gamma agonist, and niacin.

* * * * *